United States Patent
Hooke et al.

(10) Patent No.: US 8,344,627 B1
(45) Date of Patent: *Jan. 1, 2013

(54) PULSED DIELECTRIC BARRIER DISCHARGE

(75) Inventors: William McClure Hooke, Chapel Hill, NC (US); Allen Richard Martin, Hingham, MA (US); Gary Elder McGuire, Chapel Hill, NC (US); Mark Alan Ray, Raleigh, NC (US)

(73) Assignee: International Technology Center, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/329,565

(22) Filed: Dec. 19, 2011

Related U.S. Application Data

(63) Continuation of application No. 12/586,597, filed on Sep. 24, 2009, now Pat. No. 8,084,947, which is a continuation of application No. 11/980,034, filed on Oct. 30, 2007, now Pat. No. 7,615,933, which is a continuation-in-part of application No. 11/120,153, filed on May 2, 2005, now Pat. No. 7,615,931.

(51) Int. Cl.
*H05B 31/26* (2006.01)
(52) U.S. Cl. ............... 315/111.21; 315/291; 118/723 E; 204/156
(58) Field of Classification Search ............ 315/111.01, 315/111.21, 111.31, 111.71, 209 R, 289, 315/291, 360; 204/156, 164, 170; 118/723 E, 118/723 I
See application file for complete search history.

(56) References Cited

U.S. PATENT DOCUMENTS

| | | | |
|---|---|---|---|
| 3,432,633 A | 3/1969 | Anderson et al. | |
| 3,824,400 A | 7/1974 | Lehovec | |
| 4,230,994 A | 10/1980 | Bradley | |
| 4,363,774 A | 12/1982 | Bennett | |
| 5,414,324 A * | 5/1995 | Roth et al. | 315/111.21 |
| 5,508,590 A | 4/1996 | Sampayan et al. | |
| 5,651,045 A | 7/1997 | Pouvesle et al. | |
| 5,895,558 A | 4/1999 | Spence | |

(Continued)

FOREIGN PATENT DOCUMENTS
WO WO 2004/088708 A2 10/2004
(Continued)

OTHER PUBLICATIONS

International Search Report and Written Opinion, PCT/US06/15626; dated Aug. 28, 2007.

(Continued)

*Primary Examiner* — Jimmy Vu
(74) *Attorney, Agent, or Firm* — Miller Patent Services; Jerry A. Miller

(57) ABSTRACT

A method of generating a glow discharge plasma involves providing a pair of electrodes spaced apart by an electrode gap, and having a dielectric disposed in the electrode gap between the electrodes; placing the electrodes within an environment, wherein the electrode gap can be provided with a gas or gas mixture containing carbon at a specified pressure; and applying a rapid rise time voltage pulse across the electrodes to cause an extreme overvoltage condition, wherein the rapid rise time is less than a plasma generation time so that the extreme overvoltage condition occurs prior to current flow across the electrode gap. This abstract is not to be considered limiting, since other embodiments may deviate from the features described in this abstract.

30 Claims, 20 Drawing Sheets

U.S. PATENT DOCUMENTS

| | | | |
|---|---|---|---|
| 5,977,722 | A | 11/1999 | Yokokawa et al. |
| 6,059,935 | A | 5/2000 | Spence |
| 6,369,519 | B1 | 4/2002 | Okamoto et al. |
| 6,441,554 | B1 | 8/2002 | Nam et al. |
| 6,445,137 | B1 | 9/2002 | Okamoto et al. |
| 6,788,008 | B2 | 9/2004 | Hiraoka et al. |
| 6,885,153 | B2 | 4/2005 | Quon |
| 6,906,280 | B2 * | 6/2005 | Rosocha .................. 219/121.31 |
| 6,924,608 | B2 | 8/2005 | Czernichowski et al. |
| 7,095,179 | B2 * | 8/2006 | Chistyakov .............. 315/111.21 |
| 7,615,931 | B2 * | 11/2009 | Hooke et al. ............. 315/111.21 |
| 8,084,947 | B2 * | 12/2011 | Hooke et al. ............. 315/111.21 |
| 2002/0093294 | A1 | 7/2002 | Czernichowski et al. |
| 2003/0012718 | A1 | 1/2003 | Josephson et al. |
| 2004/0037736 | A1 | 2/2004 | Perruchot et al. |
| 2004/0045806 | A1 | 3/2004 | Neff et al. |
| 2004/0076543 | A1 | 4/2004 | Sokolowski et al. |
| 2004/0140194 | A1 | 7/2004 | Taylor, Jr. et al. |
| 2004/0183461 | A1 | 9/2004 | Kane et al. |
| 2005/0016456 | A1 | 1/2005 | Taguchi et al. |
| 2006/0278518 | A1 | 12/2006 | Kouznetsov |
| 2008/0106206 | A1 | 5/2008 | Hooke et al. |

FOREIGN PATENT DOCUMENTS

WO    WO 2004/088708 A3    10/2004

OTHER PUBLICATIONS

APT13GP120BDF1 Data Sheet, Advanced Power Technology, Feb. 2004.

A. V. Azarov, S. V. Mitko, and V. N. Ochkin, "An Open Barrier Discharge as Xe Laser Pumping Source," Advanced Lasers and Systems, Proceedings of SPIE vol. 5137, (2003).

A. V. Azarov, S. V. Mitko, and V. N. Ochkin, "Xe Laser Pumped by Fast Electrons Generated in a Barrier Discharge," Quantum Electronics, vol. 32, 2002.

Benedek et al., "Displacement and Emission Currents from PLZT 8/65/35 and 4/95/5 Excited by a Negative Voltage Pulse at the Rear Electrode," European Organization for Nuclear Research, Nov. 25, 1997.

Bogdanov et al., "Simulation of Pulsed Dielectric Barrier Discharge xenon excimer lamp," J. Phys. D: Appl. Phys. 37 (2004), pp. 2987-2995, Oct. 8, 2004.

Chen, "Impedance Matching for One Atmosphere Uniform Glow Discharge Plasma (OAUGDP) Reactors," IEEE Trans. on Plasma Science, vol. 30, No. 5, Oct. 2002.

Eimac Power Grid Tube—Quick Reference Data Sheet for 4PR60C/8252W, from Communication and Power Industries website, Mar. 21, 1997.

Golubovskii et al., "Study of the Homogenous Glow-like Discharge in Nitrogen at Atmospheric Pressure," J. Phys. D: Appl. Phys. 37 (2004), pp. 1346-1356, Apr. 14, 2004.

Grace et al., "Plasma Treatment of Polymers," Journal of Dispersion Science and Technology, vol. 24, Nos. 3 & 4, pp. 305-341, 2003.

A. Khacef, J. M. Cormier and J. M. Pouvesle, "$No_x$ Remediation in Oxygen-rich Exhaust Gas Using Atmospheric Pressure Non-Thermal Plasma Generated by a Pulsed Nanosecond Dielectric Barrier Discharge," Journal of Physics D: Applied Physics 35. (2002).

U. Kogelschatz, "Dielectric-Barrier Discharges: Their History, Discharge Physics, and Industrial Applications," Plasma Chemistry and Plasma Processing, vol. 23 (2003.).

J. Kohler, "Dielectric Barrier Discharge Pumped $N_2$ Laser," Applied Optics vol. 33 (1994).

Laroussi, "Nonthermal Decontamination of Biological Media by Atmospheric-Pressure Plasmas: Review, Analysis and Prospects", IEEE Transactions on Plasma Science, vol. 30, No. 4, pp. 1409-1415, Aug. 2002.

Laroussi et al., "Power consideration in the pulsed dielectric barrier discharge at atmospheric pressure," Journal of Applied Physics, vol. 96, No. 5, Sep. 1, 2004.

K. Liu, Q. Hu, J. Qiu, and H. Xiao, "A High Repetition Rate Nanosecond Pulsed Power Supply for Nonthermal Plasma Generation," IEEE Transactions on Plasma Science, vol. 33, (2005.).

Liu, et al., "Excitation of Dielectric Barrier Discharges by Unipolar Submicrosecond Square Pulses", J. Phys. D: Appl. Phys. 34 (2001), 1632-1638, 2001.

Liu, et al., "Electrical Modelling of Homogeneous Dielectric Barrier Discharges Under an Arbitrary Excitation Voltage," J. Phys. D: Appl. Phys. 35 (2003) 3144-3150, Nov. 25, 2003.

J. Mankowski and M. Kristiansen, "A Review of Short Pulse Generator Technology," IEEE Transactions on Plasma Science, vol. 28, 2000.

"OGP-Series, PGP-Series, PB-Series, Overvoltage Spark Gaps," Perkin Elmer, Inc., 2001.

Roth, et al., "The physics and phenomenology of One Atmosphere Uniform Glow Discharge Plasma (OAUGDP™) reactors for surface treatment applications," J. Phys. D: Appl. Phys. 38 (2005) pp. 555-567, Feb. 3, 2005.

A. J. Schwab and F. W. Holinger, "Compact High Power $N_2$ Laser: Circuit Theory and Design," IEEE Journal of Quantum Electronics, vol. 12, (1976).

M. Spaan, J. Leistikow, V. Schulz-von der Gathen and H. F. Dobele, "Dielectric Barrier Discharges with Steep Voltage Rise: Laser Absorption and Spectroscopy of NO Concentrations and Temperatures," Plasma Sources Science and Technology, vol. 9. (2000).

"TR-1855 External Trigger Transformer," Perkin Elmer, Inc., 2004.

"Triggered Spark Gaps, Ceramic Metal," Perkin Elmer Inc., 2001.

Trompeter, et al., "Reduction of *Bacillus subtilis* and *Aspergillus niger* Spores Using Nonthermal Atmospheric Gas Discharges", IEEE Transactions on Plasma Science, vol. 30, No. 4, pp. 1416-1423, Aug. 2002.

* cited by examiner

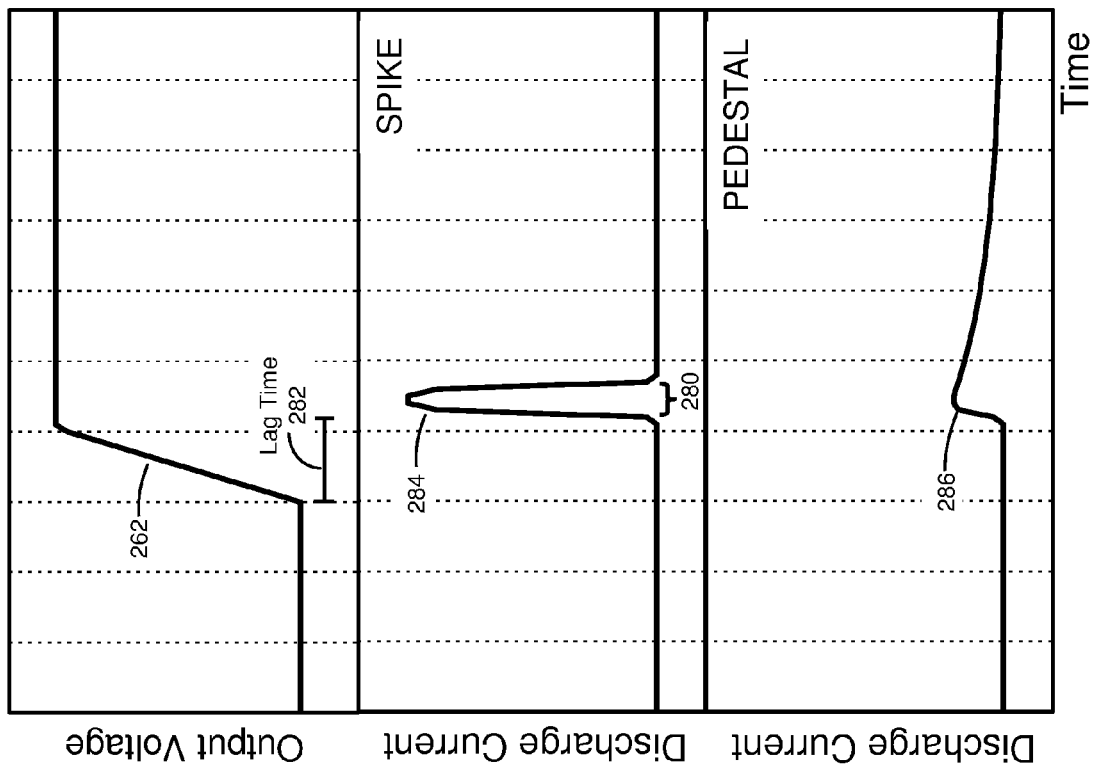

PULSED DIELECTRIC BARRIER DISCHARGE

CROSS REFERENCE TO RELATED APPLICATIONS

This application is a Continuation of allowed U.S. patent application Ser. No. 12/586,597 which is a Continuation of U.S. patent application Ser. No. 11/980,034 filed Oct. 30, 2007 which is a Continuation-In-Part of U.S. patent application Ser. No. 11/120,153, filed May 2, 2005, with priority benefit being claimed to all three applications and all three applications being hereby incorporated in their entirety by reference.

BACKGROUND

For many years, electric gas discharges have been used in a variety of applications including etching, deposition, sterilization, functionalization, etc. Commonly, these devices require sub-atmospheric pressures necessitating costly pressure locks and vacuum systems. Dielectric barrier discharge (DBD) systems, however, can operate at, below, or even above atmospheric pressure. Most DBD systems have been driven by continuous wave, radio frequency (RF), power sources. In recent years, however, there has been increased use of pulsed power sources. In comparison with the RF DBD's, pulsed power DBD's, with their greater instantaneous powers, are able to achieve higher electron and reactive species densities together with higher electron energies leading to increased exposure dosage and decreased required processing time. In addition, the pulsed systems tend to be more stable and spatially uniform than the RF DBD's. Thus devices and techniques that lead to increases in power density without excessive gas heating, arcs, or narrow filamentary discharges are of considerable value.

As noted above, one useful application of plasma discharge systems is the use of the plasma for sterilization. U.S. patent application publication number US2004/0037736 A1 to Perruchot et al., which is hereby incorporated by reference, contains an extensive background treatment in the definition of sterilization and the various sterilization methods currently known and in use. As explained by Perruchot et al., the sterilization methods that use plasma discharge systems operate by creation of reactive species such as radicals of ionized and/or excited species. Various improvements on plasma discharge sterilization methods are further discussed in Perruchot.

Dielectric barrier discharges are commonly initiated by applying an alternating voltage across a gap between two electrodes where one or both of the electrodes are covered by a dielectric barrier material. DBD are non-equilibrium discharges which typically generate electrons with mean energies of a few eV in a non-thermal background gas. The dielectric barrier serves to separate the electrode from the plasma and is required to partially inhibit the direct flow of current between the two electrodes and distribute the discharge uniformly over the electrodes. The basic principle in most cases is to produce plasmas in which a majority of the electrical energy is used for the production of energetic electrons, rather than for gas heating, hence the plasma can enhance the gas phase chemistry without having to elevate the gas phase temperature (U. Kogelschatz, Plasma Chem. Plasma P. 23, 1 (2003)).

The applied voltage is commonly established in a DBD system using an RF source such that the peak voltage is slightly greater than the threshold voltage required to establish the glow discharge. As the voltage is increased above the threshold voltage a discharge occurs between the electrodes after a small time. The time difference between the time the threshold voltage is reached and the time the discharge initiates is referred to as the lag time. Typically the voltage rise time in RF systems is large compared to the lag time, and thus slowly increasing the voltage beyond this threshold after the discharge has been initiated will not increase the voltage potential across an electrode gap.

However, if the rise-times to achieve peak voltage of the voltage pulse are shorter than the lag time between the pulse crossing the threshold voltage and the onset of the discharge, the voltage pulse will continue to increase in value towards its peak value prior to the discharge. The application of a fast rising high voltage spike is thus said to create an "overvoltage" condition prior to discharge and has been predicted to produce among other things, higher energy electrons in the discharge (Bogdanov, J. Phys. D 37, 2987 (2004)). In the parent of the present application, an extreme overvoltage condition is advantageously utilized to produce a plasma in a DBD arrangement.

To increase the potential across an electrode gap a unipolar rapid rise time rectangular pulsed voltage source using two switching modules was developed by Liu and Neiger; however, the power source they disclosed produced only limited discharge currents of a few hundred milliamps (Liu, J. Phys. D 34, 1632 (2001)). Similar results were also reported by Spaan et al. with reported discharge currents up to five hundred milliamps (Spaan, Plasma Sources Sci. Technol. 9, 146 (2000)).

Pulse-forming networks were developed by Köhler to produce single rapid rise time voltage pulses (Köhler, Appl. Opt. 33, 3812 (1994)) and Blumlein configurations have been applied to generate rapid rise time, short pulse width voltage waveforms at frequencies ranging from 1 to 1000 Hz {Pouvesle, U.S. Pat. No. 5,651,045 (1997); Khacef, J. Phys. D. 35, 1491 (2002); Liu, IEEE Trans Plasma Sci. 33, 1182 (2005)}. The limited current outputs are partially solved by Blumlein configurations, but these produce pulses defined in part by the length of the transmission lines and the impedance across the transmission lines must be matched to the load to deliver maximum power. Such impedance matching makes it more difficult to scale the output to changes in the load such as electrode size, gap distance, dielectric, and/or gases solids or liquids in the gap as might be necessary for various applications of the plasma.

BRIEF DESCRIPTION OF THE DRAWINGS

Certain illustrative embodiments of the present invention, which illustrate the method of operation, may be best understood by referring to the detailed descriptions that follow and the accompanying drawings in which:

FIG. 21, which is made up of FIGS. 21A, 21B and 21C, are plots of output voltage and discharge current for mode circuits resulting in a spiked discharge current and a pedestal discharge current.

DETAILED DESCRIPTION

Figure 1:
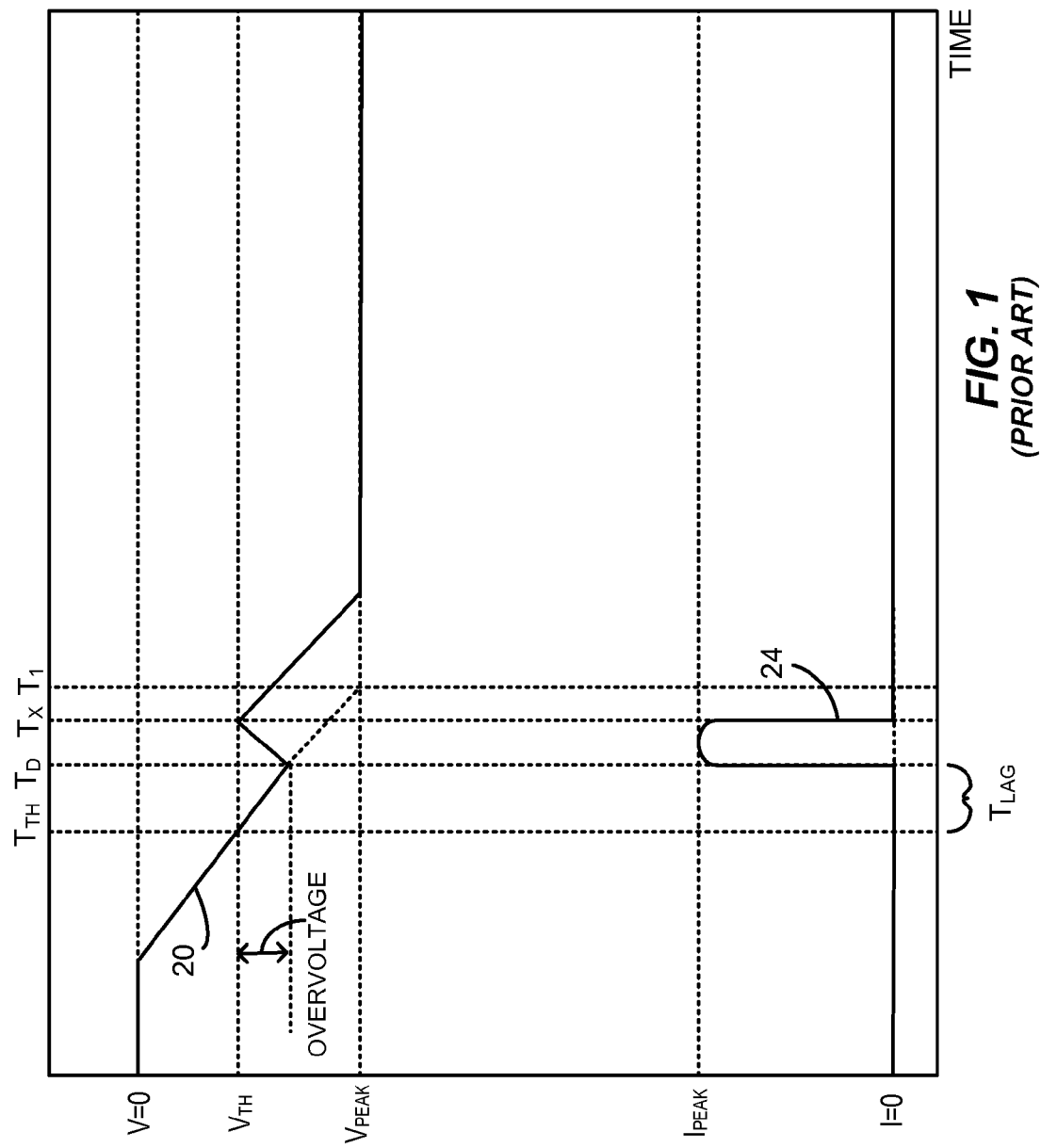
FIG. 1 is a somewhat idealized plot showing the leading edge of the voltage and current waveforms produced by a pulsed dielectric bather gas discharge (DBGD) device with slow voltage rise times.

While this invention permits the detailed embodiment in many different forms, the drawings and descriptions shown here describe a specific embodiment, with the understanding that the present disclosure of this embodiment is to be considered as an example of the principles and not intended to limit the invention to the specific embodiment shown and described. In the description below, like reference numerals are used to describe the same, similar or corresponding parts in the several drawings. Much of the discussion to follow presents theory of operation that has not yet been fully proven as of this writing. Accordingly, the invention is not to be bound by such theories advanced.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearance of such phrases in various places throughout this specification is not necessarily referring to the same embodiment. Furthermore, the particular features, structures, or characteristics may be combined in any suitable manner in one or more embodiments without limitation.

It is emphasized that the present document discloses theory of operation as currently believed and understood. However, one skilled in the art will appreciate that systems, such as the prototype embodiments described herein, can be difficult to accurately characterize until numerous operating parameters are fully explored. Accordingly, the present disclosure offers the inventors' explanations of the physical phenomenon that have been observed, with such explanations being based upon the inventors' belief at the time of this writing, but cautions the reader that the present invention is not to be bound by the theory disclosed herein as currently understood.

For purposes of this document, the following definitions will be used:

Threshold Voltage ($V_{TH}$)—the minimum voltage across the gap of a plasma generation device (glow discharge or glow-like discharge device) necessary to generate a plasma under a given pressure for a particular gas or gas mixture. This voltage varies depending upon the gas in the gap, size of the gap, gas pressure, electrode geometry and dielectric barrier characteristics.

Lag time ($T_{LAG}$)—the difference between the time the applied voltage across the gap reaches the threshold voltage ($V_{TH}$), and the time that current begins to flow in the gap.

Overvoltage—a condition in which a voltage much greater than $V_{TH}$ is rapidly applied across the gap of a plasma generation device. Overvoltage occurs during the Lag Time as described above and no current flows in the gap. A small incidental overvoltage may occur in pulsed plasma generation devices but this has a small effect unless the applied voltage is very high and the rise time is short compared to the Lag Time ($T_{LAG}$).

Extreme Overvoltage—a condition wherein a high level of overvoltage is established—generally speaking, this condition begins to manifest itself when the peak pulse voltage is greater than about 2 times the threshold voltage $V_{TH}$. It is believed that extreme overvoltage effects may be observable as low as approximately 1.5 times the threshold voltage for discharges. Such extreme overvoltage conditions are possible by using an extremely rapid rise time voltage generator that is able to achieve an extreme overvoltage condition during the lag time ($T_{LAG}$) preceding the breakdown.

Dielectric Barrier Discharge (DBD) or Dielectric Barrier Glow Discharge (DBGD)—interchangeable terms used to refer to a plasma discharge device, method or event wherein a dielectric barrier is placed between the electrodes of a plasma generation device.

Filamentary Discharge or Filaments—These terms are used to describe a discharge which has regions of high current density, typically >100 microns in diameter, with little or no discharge in the area between the filaments. This discharge is very non-uniform across the surface of the gap and is typical of many AC discharges. Filaments are also disadvantageous in general because they create non-uniformity in the plasma making the plasma's intended use less predictable and reliable.

Pulsed Plasma System or Pulsed DBD or Pulsed DBGD—a plasma generation device driven by a pulsed drive signal (as contrasted to a DC or AC (e.g., sinusoidal or RF) drive signal).

Electrode Gap or Plate Gap or simply Gap—the gap between the electrodes of a plasma generation device. A dielectric is generally interposed in the gap to prevent arcing in dielectric barrier discharge systems.

Runaway electrons—electrons which are continuously accelerated across the gap or some portion of the gap. Electrons in a discharge may undergo inelastic collisions with atoms and molecules which create ions and radicals. As the electron energy increases, the probability of collision with a gas atom decreases. At sufficiently high overvoltages, the electron energy may increase, between collisions, more than the energy that is lost when a collision occurs. Except for the collisions the electron energy continually increases as the electron accelerates in the gap or some portion of the gap (e.g., prior to a collision). This may produce electrons with up to greater than a keV of energy.

Planar Electrode—an electrode can be considered planar as opposed to a point if the electrode gap is much less than the radius of curvature of the point of the electrode.

Gas is used herein to mean either a mixture of gases including mixtures such as air, as well as a substantially pure gas such as nitrogen.

Current Spike, Initial Spike or Spike Region—the initial spike of current produced in the discharge across the gap of certain embodiments consistent with the present invention; a region of operation of a glow or glow-like discharge according to certain embodiments consistent with the present invention.

Current Pedestal, Pedestal, or Pedestal Region—a secondary surge or flow of current following the current spike produced in the discharge across the gap of certain embodiments of the present invention; a region of operation of a glow or glow-like discharge according to certain embodiments consistent with the present invention.

Plasma Generation Time—the time from the beginning of application of voltage across the gap until the time of discharge in a pulsed plasma generation system.

Sustaining Voltage—the voltage regulating properties of gas discharges. The sustaining voltage is the voltage that the discharge will fall to once breakdown has occurred.

Glow Discharge—This term, as used herein, is intended to mean both glow discharge phenomenon and glow-like discharges both of which are characterized by a uniform glow between the electrodes as opposed to spark or filamentary discharges.

Discharge—The term is used interchangeably with glow discharge, glow-like discharge, plasma discharge, or plasma.

Object or Object of Matter—This term is intended not only to embrace solid objects but also fluids, gases, liquids, semi-solids and materials in any state of matter. Thus, for example, reference to placing an object within a plasma can be interpreted to mean the same thing as exposing a liquid or gas to the plasma.

This invention, in its various embodiments, relates to dielectric barrier plasma discharges and provides for improved methods of generating high power plasma discharges with an applied overvoltage. In certain embodiments, this invention addresses a problem of generating fast voltage rise times, with current capabilities in excess of kiloamperes, across electrodes of a dielectric barrier discharge without the use of Blumleins by making use of the self-terminating behavior of dielectric barrier discharges. In certain embodiments, this invention improves upon the scalability of the output power with electrode area by generating fast rise time voltage steps for dielectric barrier discharges with internal circuit impedances less than the load impedance of the gap during discharge.

Turning now to FIG. 1, it is instructive to view an illustration of the leading edge of the voltage and current pulses of a conventional pulsed DBD system in order to appreciate the distinctions associated with embodiments consistent with the present invention. In FIG. 1, a voltage pulse 20 (shown greatly exaggerated in time so that the rise time is apparent) is applied to a pair of electrodes which have a dielectric barrier disposed between in a conventional manner. A negative-going voltage pulse is illustrated to correlate with the measurements used in tests conducted on prototypes of certain embodiments of the present invention. In this representation, a discharge occurs between the electrodes starting at time $T_D$ which interrupts the voltage waveform. The time difference between the time $T_{TH}$ the voltage reaches $V_{TH}$ and $T_D$ is referred to herein as the lag time $T_{LAG}$ as defined above. At time $T_D$, current begins to flow, as illustrated by the pulse in the current curve 24, thus establishing a brief glow discharge between the electrodes, until approximately time $T_X$. Also at time $T_X$, the voltage reaches its maximum sag as a result of the current pulse. The discharge has a peak power density that is a function of the product of the threshold voltage $V_{TH}$ and the peak current $I_{PEAK}$. In this illustration, the applied voltage drops during the current pulse as the voltage across the dielectric barrier increases. Had a discharge not occurred, the peak voltage would have been achieved at time $T_1$.

In conventional DBD devices and systems, the voltage pulse is established such that the peak voltage $V_{PEAK}$ is slightly greater than the threshold voltage $V_{TH}$ required to establish the glow discharge. Increasing the voltage beyond this threshold may have no noticeable effect upon the operation of the DBD device since the increased voltage will simply charge the dielectric barrier and terminate the discharge. As can be seen in FIG. 1, a small overvoltage may occur when applying the voltage using a slow rise time, but this is a small percentage of the pulse amplitude due to the slow rise time. Increasing the applied voltage much beyond the threshold voltage $V_{TH}$ is generally considered to be of little value. This will be true using conventional pulse generators with relatively slow rise times relative to the lag time as illustrated (and exaggerated for clarity in explanation) in FIG. 1.

One of the problems that have conventionally faced those attempting to generate plasmas using pulse generators has been that it is somewhat difficult to generate the high pulse voltages required to break down the gap. To simplify the process, the gases placed in the electrode gap are often gases that more easily breakdown such as Argon or Helium or mixtures thereof. Additionally, to make it even easier to create the discharge, such gases are often used at lower than atmospheric pressure. Such expedients have also often worked to reduce the lag time ($T_{LAG}$) between reaching the threshold voltage ($V_{TH}$) and the occurrence of a discharge. In many cases, this leads to near total elimination of the lag time, and the discharge occurs almost immediately when the voltage across the gap reaches $V_{TH}$.

Therefore, with a low pressure and relatively low breakdown voltage gas, the time lag combined with the rise time has been such that the effect of overvoltage has been entirely unexplored. DBGD systems have evolved in a manner that even if a scenario were created which caused an overvoltage condition, the level of overvoltage is somewhat self-limiting. Consider for example the overvoltage shown in FIG. 1. This overvoltage represents an extension of the rise time of pulse 20 for the duration of the lag time ($T_{LAG}$). This would create only a small overvoltage condition that has an insignificant effect on the plasma generated.

Thus, as DBGD systems have evolved, the conventional ways of thinking about how to create a discharge have had a great influence on the progress in this field. As atmospheric glow discharge systems were developed, the designs have gravitated toward the use of more easily ionized gases to relieve engineering problems associated with higher pressure devices. Many of these features naturally inhibited exploration of operational zones involving overvoltage such as those explored in conjunction with embodiments consistent with the present invention. Moreover, the difficulty in obtaining the rapid rise times and extreme voltages and currents to effect the necessary overvoltage condition has left this space unexplored.

In accordance with certain prototype embodiments consistent with the present invention, a DBD system, operating at either reduced pressure or at atmospheric pressures and driven by a high voltage, short rise time pulsed power supply, has been made that significantly exceeds the performance of known DBD systems found in the literature. The fast rise voltage pulse creates two distinct discharge regions which are referred to herein as the spike region followed by the pedestal region, as defined above. This prototype system has been shown to deliver significantly more instantaneous power (greater than one MW) than other known DBD devices. Also the additional power and total energy delivered during the pedestal current region are without known precedent. The rapid rise time is used to create an extreme overvoltage, which is the difference between the DC breakdown voltage for a specific gap distance and pressure, and the actual applied peak voltage at the time breakdown occurs. It takes a finite amount of time to breakdown the gas once the DC breakdown voltage is exceeded. For fast rise times, the overvoltage can be several times the DC breakdown voltage. This overvoltage condition is reached prior to the breakdown resulting in high levels of instantaneous power and other potentially desirable attributes as will be discussed herein.

Figure 2:
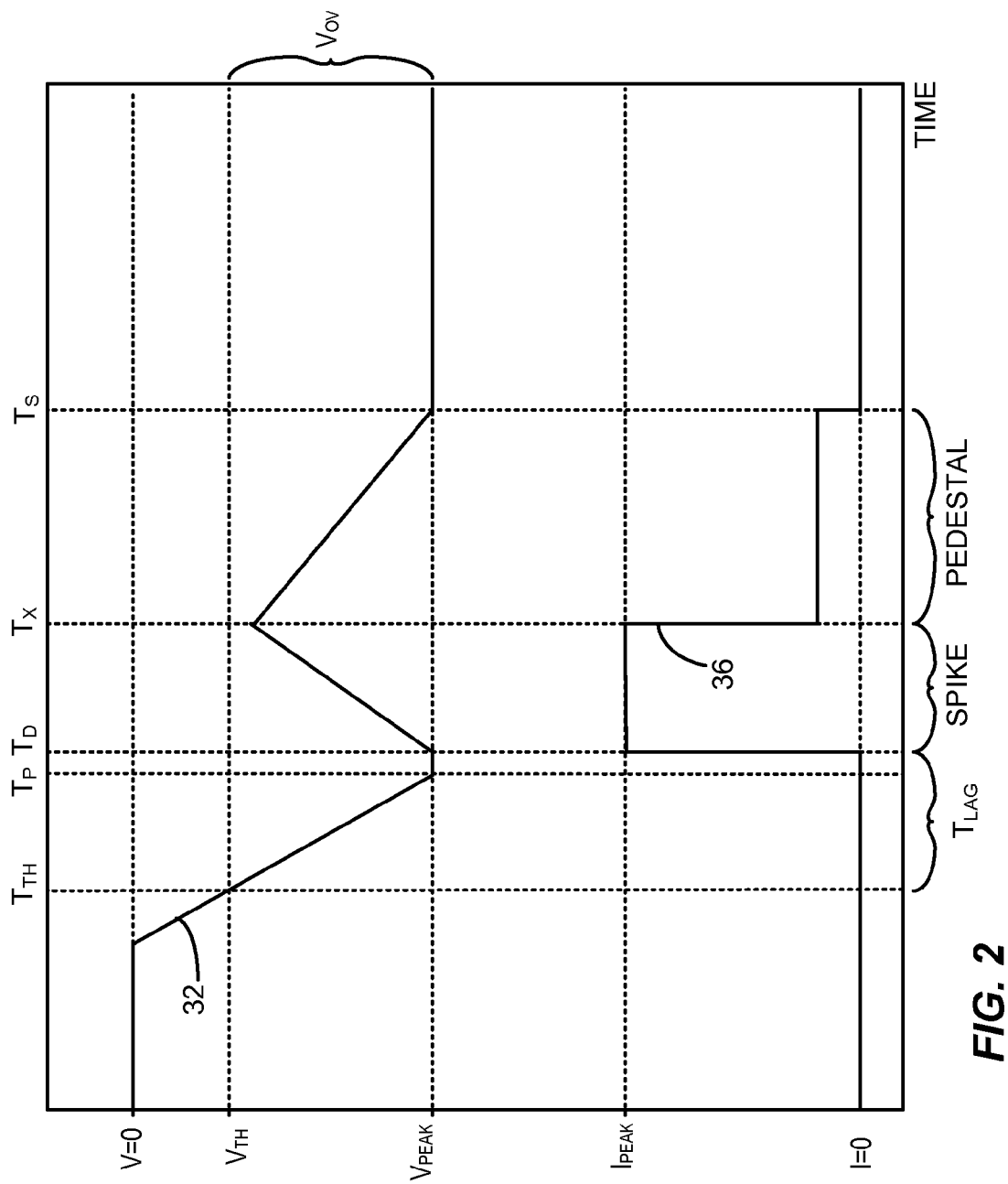
FIG. 2 is a somewhat idealized plot showing the leading edge of the voltage and current waveforms produced by a pulsed DBGD device consistent with certain embodiments of the present invention.

Referring now to FIG. 2, a somewhat idealized set of voltage and current curves (at the pulse's leading edge) for an embodiment consistent with the present invention is depicted (exaggerated rise times and operational regions). Whereas the conventional DBGD systems utilize easy-to-discharge gases, FIG. 2 illustrates some of the phenomenon which occur when more difficult-to-discharge gases are explored, although the present system is capable of operating with a wide variety of gases including the easy-to-discharge gases, using a pulse generator capable of much more rapid rise times relative to the Lag-Time than those conventionally used for this purpose. It should be noted that there is no scale associated with either FIG. 1 or FIG. 2. For purposes of this discussion, these drawings are only intended to illustrate the differences that can be obtained by using extreme overvoltage and rapid rise times.

In FIG. 2, voltage pulse 32 is applied to the electrode gap with a rapid rise time such that the threshold voltage $V_{TH}$ is reached at time $T_{TH}$ and dramatically exceeded prior to discharge time $T_D$. For purposes of discussion, a peak voltage is reached at time $T_P$ which is just prior to the time of discharge $T_D$. In this example, the peak value of the pulse $V_{PEAK}$ is shown to be approximately triple the threshold voltage $V_{TH}$, resulting in an "extreme overvoltage" condition as defined above. Generally speaking, in experiments to date, the interesting effects of overvoltage begin to manifest themselves when the peak voltage $V_P$ is about double the threshold voltage. Peak voltages $V_P$ of approximately triple the threshold voltage have been used experimentally, and even greater voltages are expected to produce even more dramatic results. Interesting effects may begin to manifest themselves at lower extreme overvoltage conditions (e.g., 1.5 times or 1.75 times the threshold voltage), but generally speaking, higher levels of extreme overvoltage generate more instantaneous power, and are thus potentially more useful. Additionally, in some instances achieving the extreme overvoltage condition may be easier when gases that are conventionally harder to break down are used.

In this illustration, it is noted that the rise time to achieve peak voltage of the voltage pulse 32 is shorter than the lag time $T_{LAG}$ between the pulse 32 crossing the threshold voltage $V_{TH}$ and the beginning of the current flow as shown by current curve 36. This permits the voltage pulse to continue to increase in value to its peak prior to the discharge at time $T_D$. Commonly, the peak voltage is generated by switching a charged capacitor across the gap. As the initial current spike is drawn from this capacitor, the gap voltage sags to approximately the gap threshold voltage. The applied voltage sags to the sum of the threshold voltage and the dielectric capacitor voltage as shown.

The initial spike region is between approximately $T_D$ and $T_X$ in FIG. 2. Following this initial spike, a pedestal region develops where current continues to flow after the initial spike and contributes substantially to the power generated. This pedestal region contains substantial energy, thus increasing the overall energy and the average power created in the discharge. The pedestal region extends from approximately $T_X$ to approximately $T_S$. The source of current for the pedestal region is apparent since the voltage waveform is seen to ramp linearly from $V_{TH}$ to $V_{PEAK}$ during this time. This voltage ramp is charging the dielectric capacitor to the peak applied voltage through the gap thereby producing the current pedestal. In certain experiments, the energy in the pedestal region has been measured to be approximately 50% of the energy delivered in the spike region, thus substantially increasing the overall energy. The approximate 50% number should not be considered limiting in any way since this percentage will vary greatly as the variable operating parameters and circuit parameters are changed.

It can be shown that the extreme overvoltage condition created by the application of substantially higher voltage prior to discharge causes breakdown to occur, and an initial spike of current to flow, at a time when the gap voltage is considerably higher than the breakdown voltage. There may be several beneficial aspects to the extreme overvoltage in certain embodiments (but no assertion is made that any or all such benefits are obtained in all embodiments consistent with the present invention). Due to the high voltages and high current densities, the product yields an extremely high instantaneous power density which greatly exceeds the power densities in known DBGD systems. Due to the pulsed nature of the discharge the gas temperature remains low with little average temperature increase, in experiments run to date.

By way of example, in experiments using the prototype system, a sheet of ordinary writing paper placed in the plasma does not exhibit discolorations with the unaided eye that might be expected from another plasma system. The gas temperature depends upon the specific operating conditions of the system such as the pulse frequency, power density, gas pressure among other things so that the average gas temperature could rise under certain operating conditions The average energy of the gas is more than 1 order of magnitude less than the average energy of the electrons. A fraction of the electrons generated in the plasma are very energetic and may be utilized as a means to cause rapid heating of surfaces under appropriate conditions. The energetic electrons are believed to be a result of the, overvoltage which provides the accelerating potential to generate the high energy electrons in the discharge, i.e., a runaway electron condition is believed to exist in the spike region.

The runaway electrons may be used in a beneficial manner for certain applications. No runaway electrons are believed to be produced in the pedestal region in experiments to date since it is believed that the gap voltage cannot be greater than the breakdown (or sustaining) voltage of the gap. In another potentially beneficial aspect, a theoretical analysis of the discharge indicates that a shock wave is created in the gas at each pulse from the pulsed voltage source. By way of inference, particles placed in a tray and exposed to the discharge are displaced; the extensive displacement of the particles is believed to be a result of the shock wave. This shock wave may be advantageously utilized for certain applications. For example, the shock wave has been observed to agitate small particles placed in the plasma. Such agitation could possibly be useful, for example, in functionalization processes to prevent the small particles from becoming agglomerated, and may facilitate more even exposure of the particles to the plasma. Again, however, it is emphasized that the actual presence of shock waves and runaway electrons are presently theorized, and that the present invention should not be limited by the current understanding of the theory of operation of the experimental prototype.

In certain embodiments consistent with the present invention, a custom designed rapid rise time pulse generator was developed in order to achieve the high voltages and currents needed to produce the desired overvoltage condition. This custom designed pulse generator, at this writing, was capable of generating voltage pulses in excess of 27 kV with a rise time of 100-350 ns. The overall plasma generation system has instantaneously generated power in the range of 800 kW to 1 MW for about 20 nS, and has produced pedestal current with power and duration on the order of 24 kW and 300 nS. This is approximately triple the voltage and five times the current of the nearest known systems at this writing. The resulting instantaneous power density is correspondingly greater. Since this power density is so much higher than other discharges described in the literature, the density of charged particles is estimated to be 1-2 orders of magnitude greater than that of other previously reported dielectric barrier discharges.

In one embodiment, the system is driven by a high voltage pulse generator which uses a switch tube to switch high voltage onto a variable parallel capacitance (in parallel with any stray capacitance), a pulse sharpener (pulse shaper), and finally the DBD system, as will be described later. It is noted that the prototype system operated without benefit of the pulse sharpener, but it is believed that use of such pulse sharpener will further enhance operation. The prototype system used for experiments described herein has two parallel plates, between which materials may be placed for etching, deposition, sterilization, functionalization, etc.

Various gases may be introduced at a controlled flow rate around the electrodes or through them by means of small holes in the plates or in a chamber surrounding the parallel plates. The parallel plates have at least one side covered with a dielectric that will withstand the applied voltage. Alumnia ($Al_2O_3$), boron nitride (BN), glass, and polyimide films such as DuPont Kapton® have been utilized in tests and proven to be hardy enough to withstand the high voltage pulsing. The best dielectric identified to date has been alumina. Higher dielectric constant materials could be used, providing they can withstand the applied voltage. A higher dielectric material is desirable because it would increase the capacitance, which in turn would store more charge and provide increased discharge duration.

Figure 3:
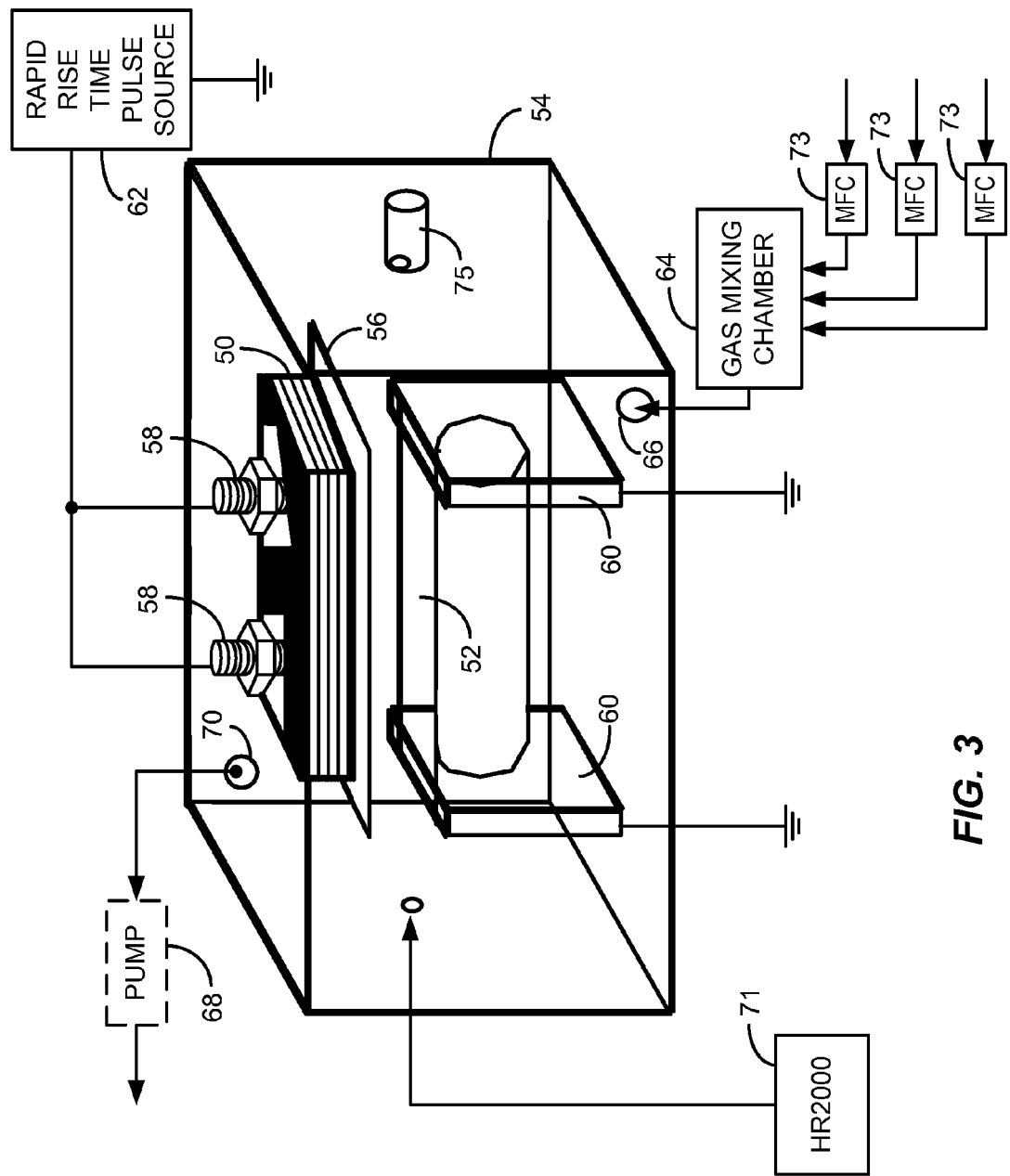
FIG. 3 is an illustration of a fixture used in the development of a DBGD consistent with certain embodiments of the present invention.

In carrying out certain of the experiments to be described, the basic test setup shown in FIG. 3 was used. In this setup, the two electrodes 50 and 52 are mounted within a chamber 54. The top electrode 50 is mounted to the upper surface of the chamber 54 with threaded studs and nuts 58. The gap can be adjusted for various experiments using the threaded studs, by shimming or otherwise adjusting the position of the top electrode plate 50 in relation to the bottom electrode 52. Gaps ranging from less than 1 mm to 8 mm have been used in experiments with this setup. The dielectric barrier 56 in this fixture is a 0.025 inch (0.635 mm) thick 4.0×4.0 inch (10.16 cm×10.16 cm) Alumina ($Al_2O_3$) plate attached to the electrode 50. The electrode as shown is rectangular, but in certain cases a circular plate, e.g., a 1.125 inch (2.858 cm) diameter plate, was used. Also, although only the upper electrode included a dielectric barrier, other arrangements such as a dielectric barrier on the bottom electrode or both electrodes have been used.

The lower electrode 52 is mounted in a rigid configuration to thermally conductive blocks that can be used to connect the lower electrode 52 to the pulse generator (or make a ground connection as shown). As originally developed, large amounts of heat were anticipated, and certain provisions were made in the fixture to provide for liquid cooling. However, the plasma generated has been quite cool, removing the need to cool the electrodes in experiments conducted to date.

In this illustration, a rapid rise time pulse generator 62 is coupled to the upper electrode and ground such that the pulses are applied across the electrode plates 50 and 52 of the fixture. Gases can be introduced and mixed in a gas mixing chamber 64 and delivered to the interior of the fixture via port 66. The gas mixture can be vented or pumped out using pump 68 through port 70. Experiments have been successfully conducted with internal chamber pressures ranging from approximately 300 Torr to approximately 1100 Torr. It is anticipated that the present arrangement could also operate at higher and lower pressures.

For the test setup, an Ocean Optics Spectrophotometer (model HR 2000) was used as an emission spectrometer to detect the species present in the plasma by resolving the plasma emission spectrum from about 200 to 1100 nm in wavelength. Mass Flow Controllers 73 or other devices can be used to control the flow of gases into the mixing chambers. In present experiments Mass Flow Meters were used to control and limit the flow of gases since the system was operated at atmospheric pressures. A port 75 is provided in the test fixture for a photodiode or other device for measuring or monitoring the optical intensity.

Figure 4:
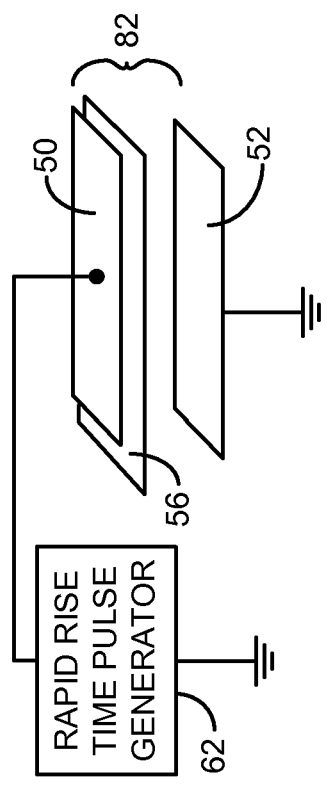
FIG. 4 is a block diagram of a DBGD device consistent with certain embodiments of the present invention.

Referring now to FIG. 4, a simplified schematic block diagram of the first embodiment of a glow discharge device is depicted. In this embodiment, the first electrode 50 has an attached dielectric barrier 56. A second electrode 52 is located below the dielectric barrier. The electrodes are separated by a gap 82. The rapid rise time pulse generator 62 is used to apply the extreme overvoltage condition to the electrodes 50 and 52 as previously described. The gap is the space between the dielectric and the lower electrode.

Figure 5:
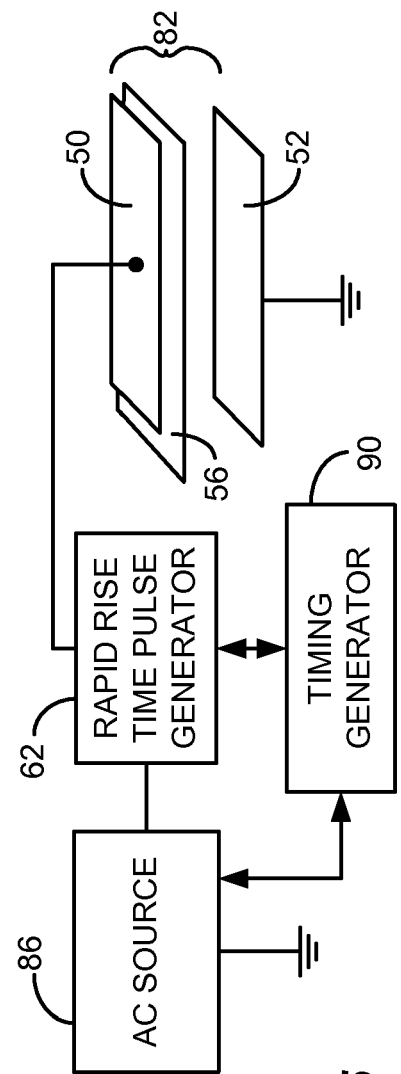
FIG. 5 is a block diagram of another embodiment of DBGD device consistent with certain other embodiments of the present invention.

Referring now to FIG. 5, an alternative embodiment is shown. By combining a low frequency RF voltage with the pulsing system, a higher extreme overvoltage condition can potentially be achieved than with the pulsing system alone. In this embodiment the phase of the pulse, relative to the RF voltage, can be controlled with a sensing and control circuit so that the pulse may be positioned at any point on the RF waveform. The combination of AC and pulsed operation raises the baseline of the pulse so that the overvoltage is increased by the amplitude of the applied RF voltage. The rapid rise time pulse generator 62 of this embodiment is used in conjunction with an AC or RF source 86 (sinusoidal, square wave, pulsed or any other suitable alternating current waveform) to apply the extreme overvoltage condition to the electrodes 50 and 52 as previously described. In this embodiment the use of the AC source 86 again is used to further increase the degree of extreme overvoltage condition appearing across the gap 82. Timing may be controlled using any suitable mechanism which derives timing for the pulses from the AC source 86.

In yet another embodiment not shown, a hybrid arrangement may be provided in which a DC offset in conjunction with an AC source and the pulse generator 62 are combined in a manner which further maximizes the extreme overvoltage condition.

Figure 6:
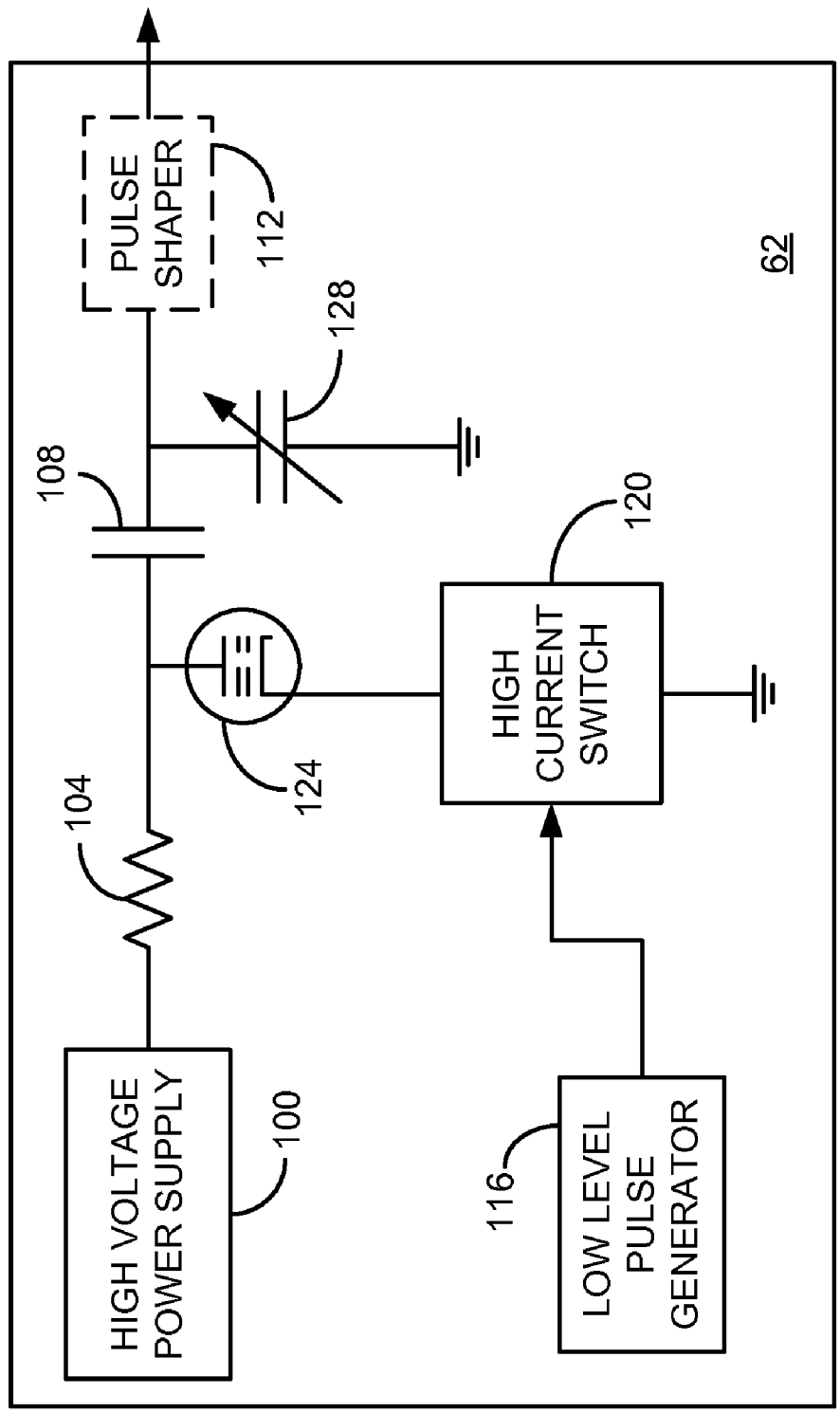
FIG. 6 is a diagram of the pulse generator 62 consistent with certain embodiments of the present invention.

FIG. 6 depicts a rapid rise time pulse generator 62 in accordance with certain embodiments of the present invention. In this embodiment, a commercial or custom designed high voltage power supply 100 is provided which produces, for example, greater than 15 KV. In the prototype embodiment, a commercial 30 kV supply was utilized. The limit of 27 kV is the maximum voltage that the switch tube was conditioned to withstand. The output of the high voltage power supply is connected to a resistor 104 (e.g., 30K ohms, 300 Watts) in series with a capacitor 108 (e.g., 0.025 µF, 30 KV). The switch tube 124 will switch the voltage on the high voltage side of capacitor 108 to ground which, in turn, reflects a negative going high voltage pulse to the output. This output is shown passing through a pulse shaper (pulse sharpener) circuit 112 (e.g., a winding on a saturable torroidal core with a bias winding used to reset the core between pulses.) which further decreases the rise time.

A low level pulse generator circuit 116 is used to control a high current switch circuit 120. The high current switch circuit grounds the cathode of a high current switch tube 124 thereby biasing the tube in a conducting state. The vacuum tube is a high voltage, high current switch tube such as an industry standard type 4PR60C (Y543) pulse tetrode vacuum tube, available from Communications and Power Industries (such as those manufactured by Eimac). The high current switch circuit is realized in the prototype using high voltage IGBT switching transistors such as industry standard number APT13GP120BDF1, commercially available from Advanced Power Technology. An adjustable or fixed capacitor 128 can also be used in parallel with the output, preceding the pulse shaper 112, in accordance with certain embodiments.

The switch tube 124 provides an initial fast rise time for the pulse and the pulse shaper refines the pulse to decrease the rise time and thereby increase the overvoltage condition. The parallel capacitance 128 (plus stray capacitance such as the plate to screen capacitance of switch tube 124) provides the initial current spike. The parallel capacitance is tunable so that the charge available for the spike can be varied depending on the application. A current transformer and high voltage probe (not shown) were used on the pulse circuit output to provide the data for the I-V curves shown later. The dielectric barrier 56 used in the experiments to be described is a 0.025 in. thick plate of high purity alumina which covers one of the electrodes (e.g., 50). A single dielectric barrier or a dielectric barrier on each electrode may be used with similar effect. The electrode area may range from as small as 1 square centimeter to several hundred square centimeters or more. The discharge characteristics as exemplified in the following traces will scale with electrode area, so long as the power supply capacity is scaled to compensate for larger electrode area. The scale factor of power with area is approximately linear.

Figure 7:
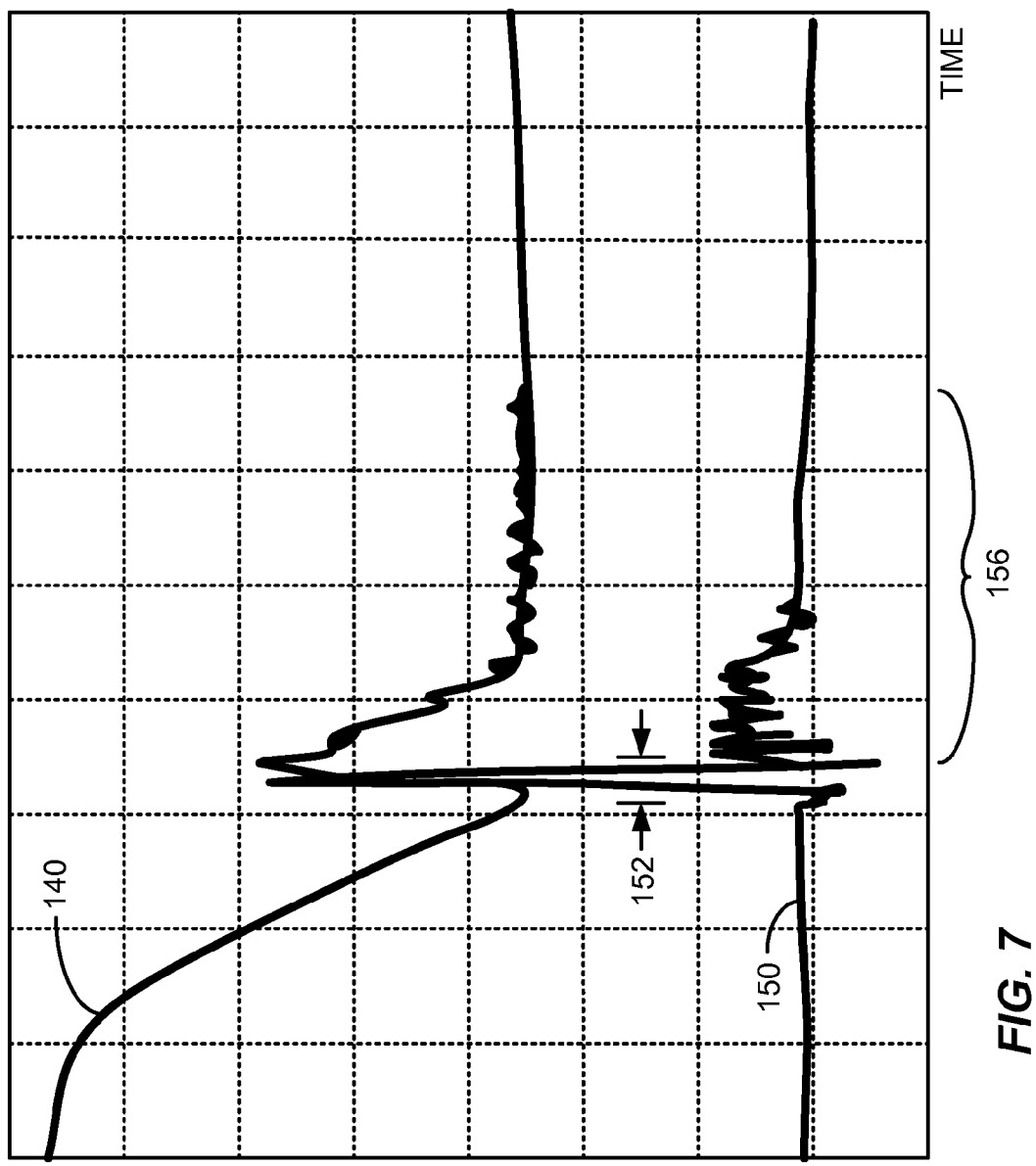
FIG. 7 is an example of the leading edge of the voltage and current waveforms using the system and methods consistent with certain embodiments of the present invention.

FIG. 7 and all traces subsequent thereto are drawings generated by reference to photographic images of actual test traces. Accordingly, they should be viewed as approximations of the actual test data. Evidence of the increased plasma power is shown in the reproduction of voltage and current traces shown in FIGS. 7-8. During these experiments, the gas used was nitrogen, the gap between the electrodes was 3.5 mm, and the dielectric was a 0.025 in thick 4.5 in×4.5 in $Al_2O_3$ plate attached to the top 1.125 in diameter circular electrode.

FIG. 7 shows a reproduction of a voltage trace 140 and a current trace 150 as obtained from actual experimental data. In this graph, the voltage scale is 5 KV/division, the current scale is 10.0 Amp/division and the sweep speed is 250 ns/division. The spike region 152 of the current pulse represents an initial spike of current through the gap during the initial part of the discharge. The spike region begins after the pulse voltage has reached its maximum value (at the end of the pulse generation time) and the end of the lag time. The pedestal region 156 begins immediately following the spike region. The widths of spike region 152 and pedestal region 156 should not be viewed as absolute from these drawings, since the drawings are illustrations of the actual voltage traces and since the actual beginning and end of such regions is difficult to identify due to the decaying nature of the trailing edges.

The extremely large spike occurs by virtue of the rapid rise time of the voltage pulse which causes the voltage to reach its maximum value before conduction begins. According to certain embodiments, the extreme overvoltage condition is achieved well in advance of the plasma generation time so that a very high voltage is achieved at breakdown. This accounts for the very high current flow once conduction in the gap begins.

Figure 8:
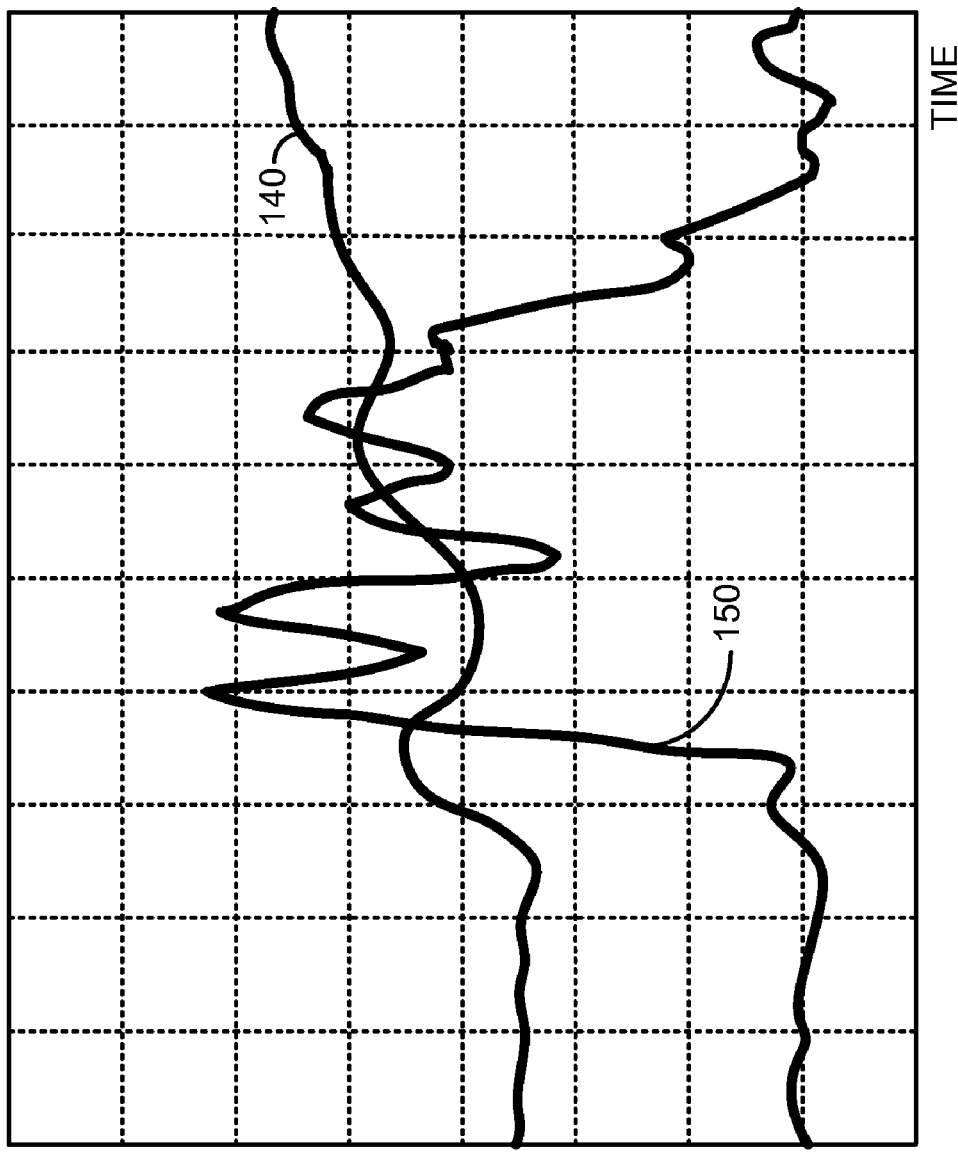
FIG. 8 is an expanded view of the waveforms illustrated in FIG. 7 using a system and methods consistent with certain embodiments of the present invention.

FIG. 8 shows an expansion of the breakdown in the spike region of the prior graph. In this graph, the voltage scale is 5 KV/division, the current scale is 10.0 Amp/division and the sweep speed is 5.0 ns/division. This illustrates that a peak current of about 40-50 A was achieved.

The traces in FIG. 7 show the high current spike at 152 followed by the pedestal current region 156. During the initial part of the current spike, as shown in FIG. 8, the current increases rapidly while the voltage begins to ramp down in accordance with the integral of the current waveform divided by the parallel capacitance. From analysis of the schematic of FIG. 6, it can be seen that the voltage drops because the stray capacitance and parallel capacitance discharges into the gap. The voltage decreases until the spike ends. The pulsed power supply then replenishes the charge on the parallel capacitor after the spike, and in the process it produces the pedestal current region. Once the dielectric capacitor is fully charged (to approximately the pulse voltage) all the currents decay to zero until the next pulse. The voltage decrease in the spike region and the voltage increase in the pedestal region are approximately linear as a function of time.

Figure 9:
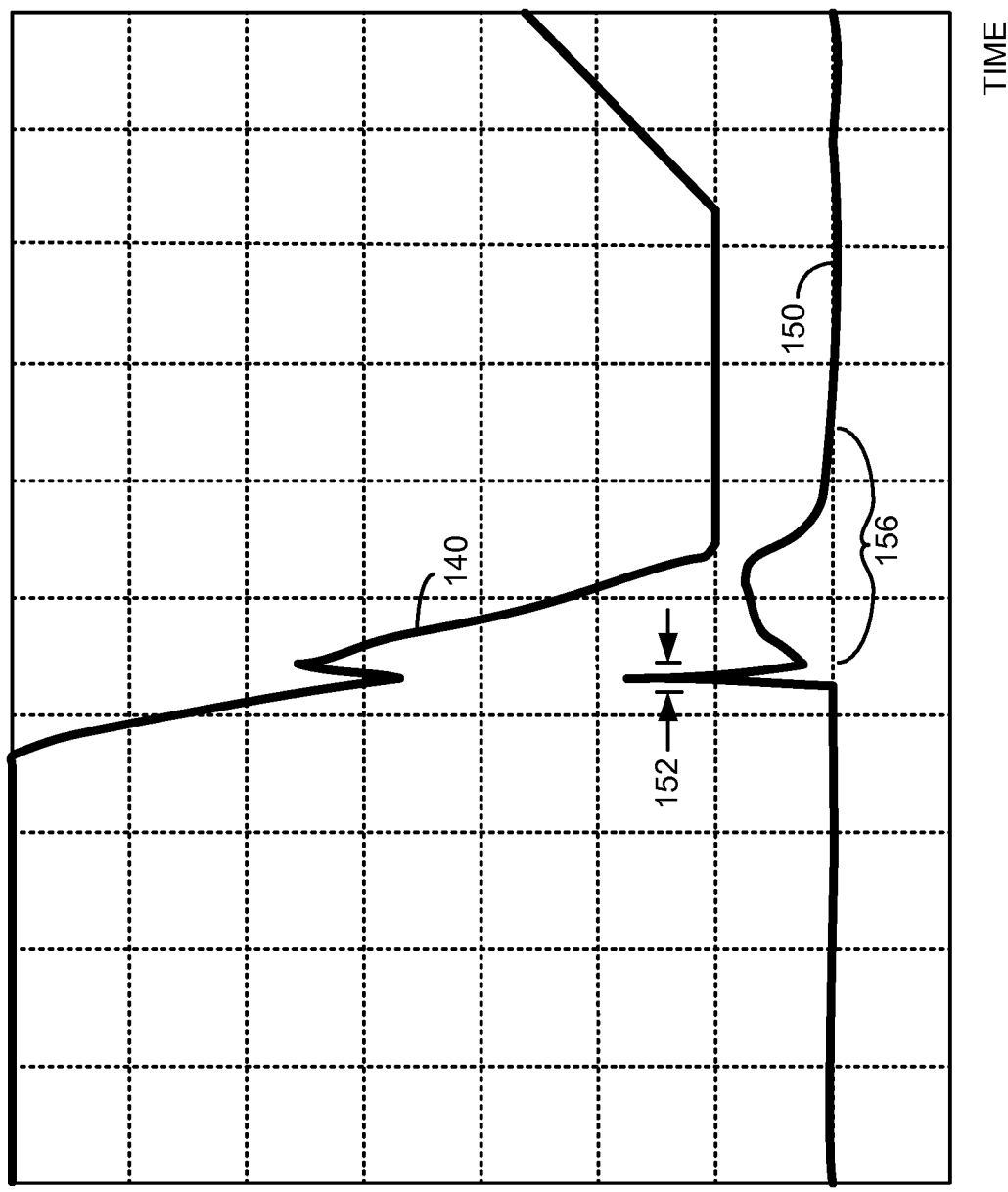
FIG. 9 is a second example of voltage and current traces using different operating conditions with the system and methods consistent with certain embodiments of the present invention.

The plasma formed by the pulse is very uniform, as observed by eye, with slight variations in current density across the surface. The variations in current density are much smaller than for filamentary discharges and any filamentary discharges that do occur do not remain in a fixed position at the electrode. The variations in the discharge will lead to many stochastically spaced spikes on the current trace. The uniformity can be seen in the current waveforms after a short conditioning period that is believed to remove impurities from the electrodes. An exemplary uniform glow waveform after conditioning is depicted in FIG. 9. The average current in the pedestal in this case is approximately 7-8 A for about 350 ns. In this trace, the current spike is relatively small because the overvoltage was small. In this case, operating parameters were adjusted to cause early breakdown on the leading edge with minimum overvoltage. However, even at the lower overvoltage condition the current waveform is very smooth, which indicates that the discharge is uniform. This set of curves was generated at a pulse repetition frequency of 300 Hz and is typical of data taken for up to 5000 Hz. In FIG. 9, the voltage scale is 5 KV/division, the current scale is 10.0 Amp/division and the sweep speed is 500 ns/division.

Figure 10:
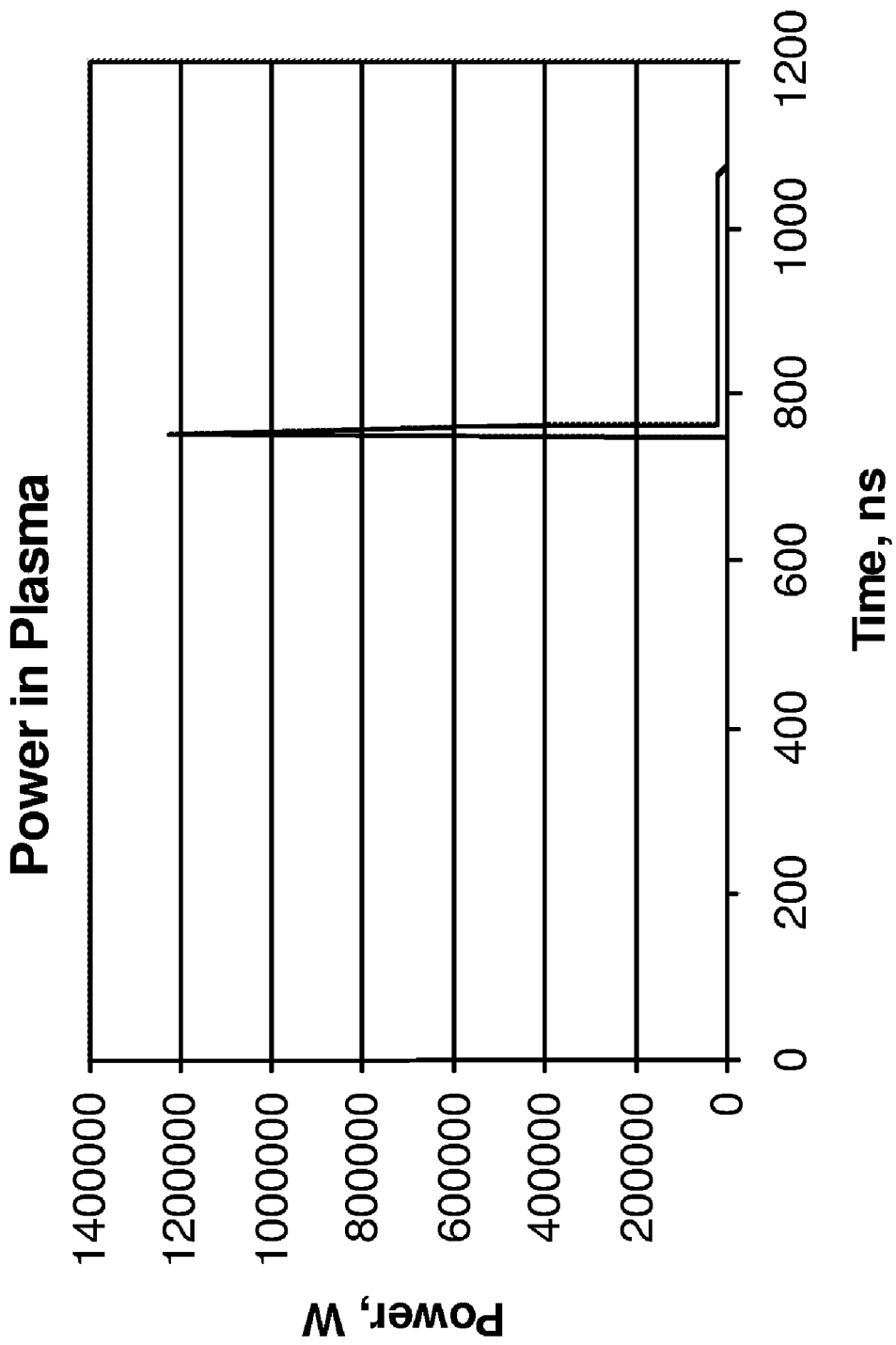
FIG. 10 is a graph of instantaneous power delivered to the discharge in an experiment carried out with a system and methods consistent with certain embodiments of the present invention.
Figure 11:
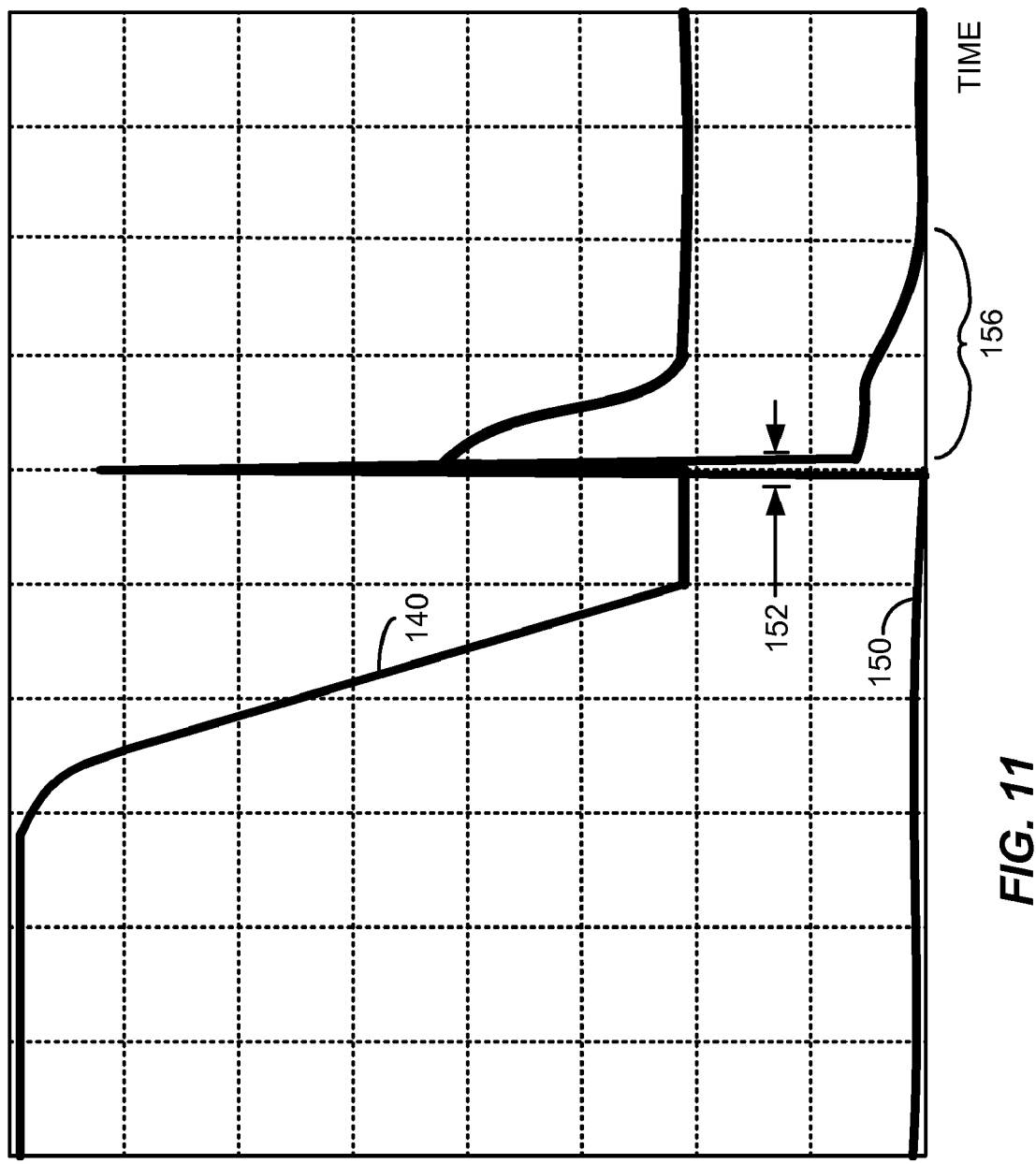
FIG. 11 is another example of the voltage and current waveforms for an experiment carried out with the system and methods consistent with certain embodiments of the present invention.

The uniformity in the current waveform is also evidence of the uniformity across the discharge area. The discharges appear to be at least as uniform as the glow-like discharges described by Golubovskii et al. (Yu B. Golubovskii et al., J. Phys. D: Appl. Phys 37, 1346, 2004) who worked at significantly lower voltages and power levels. The small number of filamentary discharges that are seen appear to be stochastically distributed in space and time and thereby do not remain fixed. As a result, the small number of randomly distributed filamentary discharges contribute very few (if any) localized effects on the substrate surface From an analysis of the schematic and a typical I-V curve, the power input into the discharge is approximated in the graph of FIG. 10. The instantaneous power in the plasma is based on the calculated voltage of the gap, and the I-V curves reproduced in FIG. 11. The energy deposited in the discharge by the spike and the pedestal regions are approximately equal (within a factor of 2). In FIG. 11, the voltage scale is 5 KV/division, the current scale is 10.0 Amp/division and the sweep speed is 250 ns/division.

Power such as that shown above is achieved from a system which was built to achieve fast rise time and deliver substantial current at breakdown. The fast rise time allows an extreme overvoltage condition to be developed prior to the discharge. The extreme overvoltage is responsible for the high current spike into the discharge. Increased current densities help to make the discharge more uniform. Generally speaking, the usefulness of a DBD is directly related to the dose of activated species in the plasma. The dose is the energy density or power per unit area multiplied by the time. The exceedingly large power densities in this plasma promise to make it much more effective in certain applications than most systems found in the literature.

The average energy of the electrons in the discharge is significantly higher than in other DBD systems that do not have extreme overvoltages. At sufficiently sharp rise times and overvoltages, runaway electrons are believed to be produced. (Runaway electrons are the fraction of electrons which undergoes continuous acceleration across the gap.) The threshold for runaway electrons in nitrogen, in terms of electric field/pressure, is approximately 150V/cm-Torr. The prototype used for the experiments described above can operate in the 190,000V/cm regime in nitrogen, which corresponds to approximately 250V/cm-Torr. This electric field/pressure is sufficiently high to produce runaway electrons with enough potential to produce x-rays. The ions, radicals, metastables, and other excited atomic and molecular species are limited to low energies due to their larger mass and due to energy loss as a result of collisions with neutral gas particles.

Without a fast rise time (i.e., fast enough to produce extreme overvoltage prior to the discharge), no extreme overvoltage can occur and the discharge is limited to DC breakdown voltages. The most efficient discharge in terms of overall current, excited species, high dose etc. is expected to be a pulsed system with a fast rise time. The plasma system described can be operated at atmospheric pressure (as well as other pressures) using $N_2$, air, $O_2$, Ar, Kr, Ne, He, $SF_6$, $CF_4$, $CO_2$, CO, acetylene, or any mixture of these or many other gases.

The use of $SF_6$ highlights the benefit of using the fast rise time pulsed system. $SF_6$ is a high dielectric constant gas with a high breakdown voltage and is frequently used to stop discharge formation. Its breakdown voltage is higher than the breakdown voltage of the other gases mentioned. It is thus a very difficult gas in which to produce a glow discharge. However, as with all gases tested, a high current discharge in $SF_6$ was easily obtained using the present prototype system. All gases examined have produced acceptable results as a discharge gas. The discharge can also be operated under vacuum or even higher than atmospheric pressures. Certain benefits of systems such as the prototype system described are best seen at higher pressures, but embodiments consistent with the present invention are in no way limited to any pressure range. Atmospheric pressure and air may be of particular interest in certain embodiments since processes can be carried out without the necessity of evacuation of the chamber and filling with a specified gas mixture, while other applications may require the presence of a particular gas.

A range of possible applications for this plasma technology is listed below. Plasma systems have been used in many of these instances, while others of the applications are merely theorized at present, and it is anticipated that the present plasma system can similarly be used. Such applications include, but are not limited to, plasma sterilization, blood plasma sterilization, ozone generation, Excimer lamps and lasers, surface modification and functionalization, surface cleaning of organic residues, reactive ion etching of materials, plasma enhanced chemical vapor deposition of materials, enhanced atomic layer deposition, enhanced catalysis, plasma polymerization, hydrogen production by stripping hydrogen from larger molecules, plasma displays, air pollution abatement and remediation, to mention a few. Systems consistent with the present invention can be used in combination with other apparatus such as a substrate heater, a sample loading system, or a continuous feed system for processing rolls of material. One example would include sterilization of coated paper product surfaces (e.g., milk carton material).

In accordance with certain embodiments consistent with the present invention, the plasma voltage and current traces show a spike formed at the start of the discharge, followed by a pedestal current region that continues until the dielectric is fully charged. The discharge then shuts off. This is in contrast to other systems in which the current shuts off immediately after the original spike. The extreme overvoltage undergoes a voltage decrease during the initial spike. The power supply then replenishes the voltage and thereby produces the pedestal current region in the gap. The pedestal region appears to be unique to systems with such an extreme overvoltage condition and robust power supply.

The extreme overvoltage occurs because the voltage rise time is fast enough for the voltage to reach extreme overvoltage during the lag time preceding the formation of the discharge. Thus the voltage applied across the electrode gap is substantially greater than the normal DC breakdown voltage at any electrode spacing. This helps produce a normal, glow-like plasma and avoids the generation of high current filaments. Filaments are easily formed in low current discharges because, small areas of the dielectric may be charged independently. At very high current densities, there is no chance for widely separated charges to funnel into a single point. Dumping the total charge on the dielectric, in effect, forces the spreading of charge in a uniform manner across the surface.

In accordance with certain embodiments, various attributes of the discharge have been observed and these can be enhanced to suit the requirements for particular applications. Many of these attributes may be advantageous for various applications. By way of example, and without any suggestion that any or all of the present attributes are necessary conditions which are present in any given embodiment, the following observations (and associated theories) are presented:

1. The DBD discharge created by the pulsed system forms two distinct plasma regions which are a.) an initial high current spike, followed by b.) a longer duration lower current pedestal region.
2. The above prototype has demonstrated the highest known instantaneous power in the spike region. Instantaneous discharge power of $\geq 1$ MW in the spike region and instantaneous discharge power of $\geq 23$ kW in the pedestal region have been achieved.
3. The large spike power appears to be due to the overvoltage created by the fast rise time of the pulsed power supply and the parallel capacitance in the system which discharges rapidly into the gap. Tuning the parallel capacitance should permit variation in the size and shape of the initial spike. This allows tuning of the spike for various applications.
4. A pulse sharpener can be used to decrease the rise time, thereby increasing the overvoltage, and thereby increasing the spike and pedestal power.
5. The noted pedestal region's instantaneous and total power is unprecedented. The pedestal region is created because the power supply must replenish the voltage that is initially discharged in the spike region. The prototype power supply design is believed to provide the rapid voltage replenishment which gives rise to a pedestal current.
6. To date, the highest DBD current density achieved has been approximately 10 A/cm$^2$. This is dramatically higher than known systems are able to produce. More power means higher dose and faster operation for most applications.
7. The high peak power and low average power in the system provides substantial instantaneous gas heating, while the average gas temperature and work-piece can be kept cool.
8. The system can be scaled almost linearly with electrode size, i.e., the characteristics of the plasma will be nearly identical if the available power is scaled with the electrode area.
9. The sharp rise time which produces the extreme overvoltage is also believed to increase the average electron energy some of which attain high electron energies which are believed to be runaway electrons. This system is believed to produce runaway electrons which may provide beneficial aspects in certain applications such as plasma sterilization.
10. The runaway electrons produced when an extreme overvoltage condition is used to produce the plasma are believed to have the necessary energy to produce x-rays.
11. A combined RF and pulsed power supply can potentially be used to achieve higher overvoltages without altering the pulse generator. This increases the power to the pulses and increases the energy of the electrons. A synchronizer can be used for timing the generation of pulsed voltage so that pulses are applied at the most beneficial part of the RF voltage waveform.
12. The high voltage attainable with this system provides a larger working distance (gap) than with known conventional RF DBD systems. A working gap of 7-8 mm has been used successfully during nitrogen plasma generation using the present pulsed mode power supply.
13. The prototype DBD system appears to be capable of using virtually any gas and has been used with the following gases and mixtures of gases: $N_2$, air, $O_2$, Ar, Kr, Ne, He, $SF_6$, $CF_4$, $CO_2$, CO, and acetylene.
14. A shock wave is believed to be created in the plasma due to the deposition of power in the working gas over a shorter time than the acoustic transit time in the gas. Therefore, in some instances, a container is required to contain small particles being treated so that the shock wave does not move them from the working area. As noted, this shock may be useful for agitation or other purposes.

Figure 12:
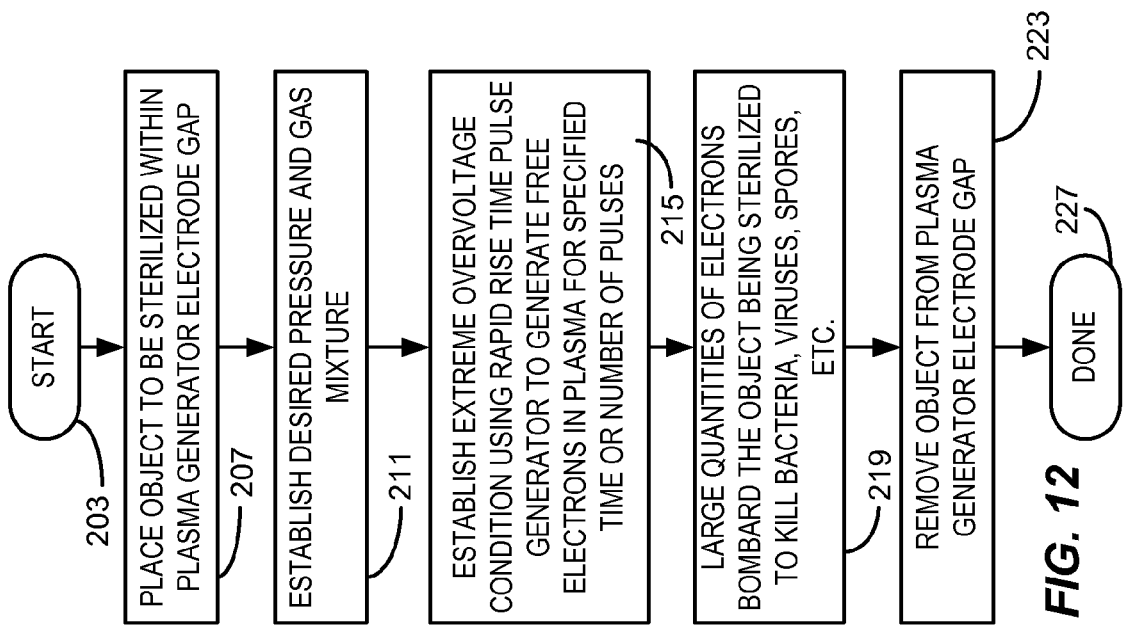
FIG. 12 is a flow chart of a sterilization process consistent with certain embodiments of the present invention.

Embodiments consistent with the present invention may be well suited for sterilization applications. In order to achieve sterilization, a process such as that depicted in FIG. 12 can be used, starting at 203. An object of matter (whether solid, liquid, gas, etc.) to be sterilized is placed within the gap of the plasma generator at 207. A desired mixture of gases is provided at 211 as an environment for the discharge. In experiments to date, the gas environment does not seem to be critical. An extreme overvoltage condition is then created across the gap by using a rapid rise time pulse generator at 215. This process has been used to treat the object at 219 and to kill bacteria and possibly other virulent biological materials. After a prescribed time, which can be determined experimentally, the sterilized object can be removed from the electrode gap at 223. The process ends at 227. It is believed that the electrons produced in the system are responsible for the very rapid sterilization. This is the first known use of electrons extracted from a plasma to achieve sterilization.

Sterilization has been successfully carried out using the prototype device described above. Consider, for example, the following experiments:

EXAMPLE

Figure 13:
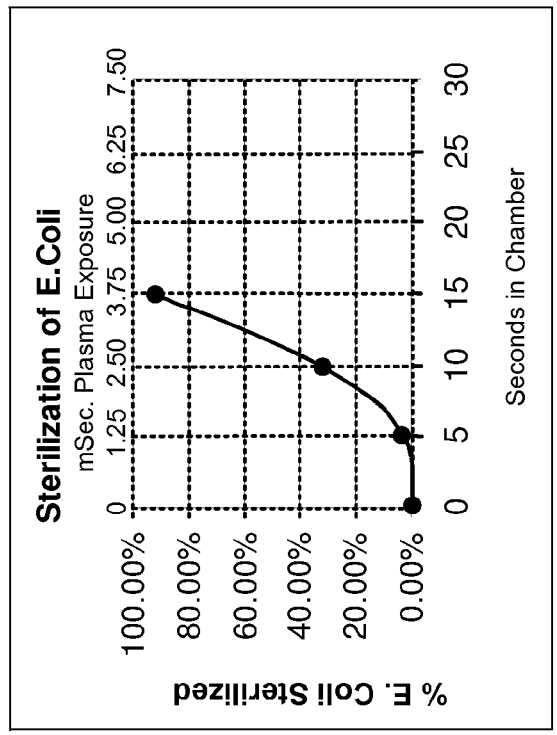
FIG. 13 is a graph illustrating the sterilization of *E. coli* that occurred in a sterilization experiment carried out with the system and methods consistent with certain embodiments of the present invention.

An example of the effects of sterilization is given below. An experiment on *E. Coli* bacteria was performed using a nitrogen plasma operated at 22 kV, a 3-4 mm electrode gap spacing, approximately 10 A spike current and approximately 2 A peak pedestal current. The pulse repetition rate was approximately 300 pulses per second, thus the overall exposure to the plasma represents a relatively small percentage of the time. *E. Coli* was deposited on polystyrene substrates and exposed to the plasma for 5, 10, and 15 seconds total time. Other samples were exposed for minutes rather than seconds. When cultured using an agar solution for 3 days at room temperature, the control samples showed on average 500 colonies of bacteria on the surface. When the exposed samples were cultured using the same conditions, the results are shown in FIG. 13. All exposures greater than approximately 30 seconds resulted in no detectable colonies. As can be seen from the graph of FIG. 13, the actual time of exposure to the plasma for each test sample was approximately 1.25 mS, 2.5 mS and 3.75 mS respectively for 5, 10 and 15 seconds of total time of operation. Thus, in a more optimized system, actual time of exposure could be dramatically shortened by increases in the pulse repetition rate.

Sterilization using plasma discharges based on the generation and utilization of ions, ozone, and ultraviolet (UV) radiation is known. In a nitrogen plasma 316 nm is the lowest energy UV wavelength observed. Based upon the literature UV exposure at this energy does not account for this dramatic reduction of the bacteria population in this short exposure time. Ozone exposure, and thermal exposure, both well known methods of sterilization, do not appear to account for the dramatic reduction of the bacteria population in this short period of exposure since only trace amounts of oxygen containing gases are present and the average gas temperature remains low. It is believed that the average ion energies in the plasma are very low and not sufficient to completely penetrate the cell walls. Ions could erode the cell wall through ion sputtering given enough time at low energies. There are accounts of the use of reactive gases in the plasma to generate ions and free radicals that are chemically very reactive and which quickly react with and erode the cell wall. However, nitrogen has not been described for this purpose because it is well known that nitrogen is not as corrosive to organic materials as oxygen, hydroxide, or other oxygen bearing species are. It is therefore believed that the cause of the sterilization is bombardment of the cells by electrons that penetrate and destroy the cells.

Two anecdotal experiments appear to further confirm this hypothesis. In these experiments, sterilization of *E. Coli* was carried out in an inoculated culturing media manufactured by 3M corporation in one experiment. In another experiment, samples of 3 ml of water were sterilized using the plasma. In the water experiment, it was observed that the water moved and flattened out into a film during exposure to the plasma. In both cases, sterilization was achieved. It is believed that the electrons have the requisite energy and are responsible for the observed sterilization.

Thus, a dielectric barrier plasma discharge device consistent with certain embodiments of the present invention has a pair of electrodes spaced apart by an electrode gap. A dielectric is disposed between the electrodes. The electrode gap is provided with a gas at a specified pressure. A rapid rise time voltage pulse generator produces a voltage pulse across the electrodes to cause an extreme overvoltage condition, wherein the rapid rise time is less than the plasma generation time so that the extreme overvoltage condition occurs prior to current flow across the electrode gap. The resulting plasma can be utilized to carry out many potential tasks including, but not limited to sterilization.

A method of generating a glow discharge plasma, consistent with certain embodiments hereof involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage condition, wherein the rapid rise time is less than a plasma generation time so that the extreme overvoltage condition occurs prior to current flow across the electrode gap.

A method of generating a glow discharge plasma for sterilization consistent with certain embodiments involves providing a pair of electrodes spaced apart by an electrode gap, and having a dielectric disposed in the electrode gap between the electrodes; placing the electrodes within an environment wherein the electrode gap can be provided with a gas at a specified pressure; applying a rapid rise time voltage pulse across the electrodes to cause an extreme overvoltage condition, wherein the rapid rise time is less than a plasma generation time so that the extreme overvoltage condition occurs prior to current flow across the electrode gap; and exposing an object of matter to the plasma for a specified time, thereby sterilizing the object.

A dielectric barrier plasma discharge device consistent with certain embodiments has a pair of electrodes spaced apart by an electrode gap. A dielectric is disposed between the electrodes. The electrode gap is provided with a gas at a specified pressure. A rapid rise time voltage pulse generator produces a voltage pulse across the electrodes to cause an extreme overvoltage condition, wherein runaway electrons are generated in the plasma.

A method of generating a glow discharge plasma consistent with certain embodiments involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage condition wherein a runaway electron condition is generated in the electrode gap.

A dielectric barrier plasma discharge device consistent with certain embodiments has a pair of electrodes spaced apart by an electrode gap. A dielectric disposed between the electrodes. The electrode gap is provided with a gas at a specified pressure. A rapid rise time voltage pulse generator produces a voltage pulse across the electrodes to cause an extreme overvoltage condition, wherein a shock wave is produced in the plasma.

A method of generating a glow discharge plasma involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage condition wherein a shock wave is generated in a plasma generated in the electrode gap.

A dielectric barrier plasma discharge device consistent with certain embodiments has a pair of electrodes spaced apart by an electrode gap. A dielectric disposed between the electrodes. The electrode gap is provided with a gas at a specified pressure. A rapid rise time voltage pulse generator produces a voltage pulse across the electrodes to cause an extreme overvoltage condition, whereby, current flowing between the electrodes can be characterized by an initial spike in current followed by a pedestal region wherein current continues to flow after the initial spike in current.

A method of generating a glow discharge plasma involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage, whereby, current flowing between the electrodes can be characterized by an initial spike in current followed by a pedestal region wherein current continues to flow after the initial spike in current.

A method of sterilizing an object of matter in a manner consistent with certain embodiments involves generating a plasma exhibiting a runaway electron condition; and exposing the object of matter to the plasma for a specified time, whereby the object is bombarded with high energy electrons to sterilize the object.

In the above methods and apparatus, it is thus believed that an object can be exposed to the plasma for a specified time, in order to effect at least one of the following: plasma sterilization, blood plasma sterilization, Ozone generation, surface modification and functionalization, surface cleaning of organic residues, reactive ion etching of materials, plasma enhanced chemical vapor deposition materials, enhanced atomic layer deposition, enhanced catalysis, plasma polymerization, surface heating, hydrogen production from stripping of hydrogen from larger molecules, plasma displays, air pollution abatement and air pollution remediation. It is further believed that generating excited species in the plasma can be used to produce one of the following: an Excimer lamp, lasers, and a $CO_2$ lasers.

In various actual experiments conducted, Helium, Nitrogen, Argon, Krypton, $CF_4$, $SF_6$, Acetylene, $TiCl_4$, and air were all easily discharged at atmospheric pressures. It is thus believed that any number of gases can be utilized, including but not limited to: air, Sulfur Hexafluoride (SF6), Nitrogen, Oxygen, Carbon Tetrafluoride ($CF_4$), Acetylene, Helium, Neon, Argon, Krypton, Xenon, or mixtures of any of these gases.

Etching gases that can potentially be used include Fluorinated gases for semiconductor etching applications may be used such as $CF_4$, $SF_6$, $CHF_3$, Nitrogen Trifluoride ($NF_3$), and Hydrofluoric Acid (HF). Also chlorinated gases used for etching applications such as Boron Trichloride ($BCl_3$), Chlorine ($Cl_2$), and Hydrochloric Acid (HCl). Also hydrogen containing gases used in etching such as Hydrogen ($H_2$), Ammonia ($NH_3$), Methane ($CH_4$), and alcohols such as Methanol ($CH_3OH$) can potentially be used. Gases for the PECVD of Si may potentially be used such as Silane ($SiH_4$), Disilane ($Si_2H_6$), and Dichlorosilane ($SiH_2Cl_2$), Tetraethylorthosilicate (TEOS) and other ortho silicate gases.

Other gases for the deposition of semiconductor materials such as germane ($GeH_4$), zinc chloride ($ZnCl_2$), dimethylzinc (DMZn), trimethylgallium (TMGa), gallium trichloride ($GaCl_3$), hydrogen sulfide ($H_2S$), and arsine ($AsH_3$) can also potentially be used.

Metal containing gases for metal deposition such as tantalum pentafluoride ($TaF_5$), tungsten hexafluoride ($WF_6$), titanium tetreachloride ($TiCl_4$), molybdenum hexafluoride ($MoF_6$), aluminum chloride ($AlCl_3$), aluminum acetylacetate, copper acetonylacetonate, nickel acetate, nickel carbonyl, hafnium chloride ($HfCl_4$), and other metal containing gases can potentially be used. Carbon containing gases such as methane, ethane, propane, etc. can potentially be used.

Gases that are useful in sterilization such as oxygen, nitrogen, air, ozone, HCl, KOH or mixtures of these gases can potentially be used.

Functionalization can potentially be carried out using for example the fluorinated gases such as $SF_6$, $CHF_3$, $CF_4$, to add F to surfaces or gases containing hydroxyl groups such as acetic acid, water, alcohols, or other larger molecular groups to add hydroxyl groups to surfaces.

Other gases that are not readily available in the gas phase may be boiled from the liquid phase and introduced into the plasma system. For example water may be boiled to produce steam which can be introduced to the chamber with or without a carrier gas. To summarize, the gas used is dependent upon the work that is desired to be carried out by or in the plasma. Many other gases may be used without limitation.

Figure 14:
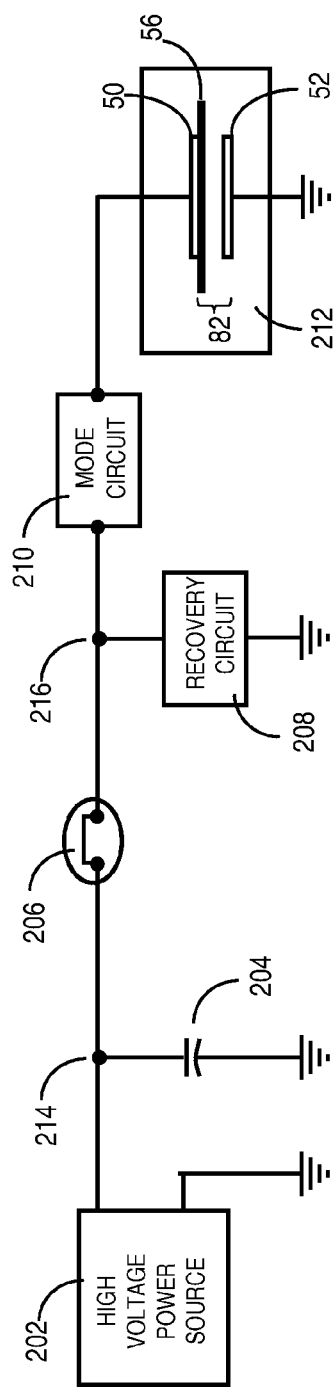
FIG. 14 shows a block diagram for a method of generating a fast rise time output voltage step consistent with certain embodiments of the present invention.

Another embodiment consistent with the present invention is depicted in the simplified schematic block diagram showing an apparatus for generating fast voltage rise times, with high current capabilities for plasma generation in dielectric barrier discharge plasmas is drawn in FIG. 14. In this embodiment, a high voltage power source 202 is used to charge one or more high voltage capacitors in a storage capacitor bank 204. The term "capacitor bank" is used in this context to mean one or more capacitors arranged in any series and/or parallel configuration to produce a desired level of capacitive storage of energy while withstanding the very high voltages (e.g., 10-60 kV or greater) produced by the high voltage DC power supply 202. In prototypes, a bank of four capacitors—two sets of series capacitors arranged in parallel, were used to produce 0.03 microfarads of capacitance with a voltage rating of 70 kV, but a single capacitor or other capacitor arrangements could similarly be used without limitation. With all embodiments, due to the high voltages and currents being used, due care is to be exercised in properly arranging wiring, use of conductors with large surface area, and cautious circuit arrangement to prevent arcing, wire burnout and other dangerous phenomenon.

In parallel with the storage capacitor bank is a switching device 206 to the load. The switching device 206 will not conduct until either triggered and/or the difference between voltages at supply side test point 214 and load side test point 216 exceeds the threshold voltage of the switching device, depending upon the nature of switching device 206.

The output of switching device 206 is connected to a recovery circuit 208, a mode circuit 210, and a dielectric barrier discharge circuit 212. The function of the mode circuit 210 and the recovery circuit 208 will be discussed later. The embodiment of the dielectric barrier discharge circuit depicted in FIG. 14 has a first electrode 50, a dielectric barrier material 56 attached to the first electrode, and a second electrode 52. The dielectric barrier material and the second electrode in this embodiment are separated by a discharge gap 82 that can range from, for example, about one tenth of a millimeter to several tens of millimeters (e.g., up to about 40-50 mm) in spacing at atmospheric pressures with a preferred spacing being dependent upon the specific application of the discharge being produced.

Once switching device 206 begins conducting, the voltage at the load side test point 216 rises as does the voltage at the first electrode 50. The rise time of the voltage at the load side test point 216 and the first electrode 50 is sufficient to generate an extreme overvoltage condition within the lag time and subsequently a plasma discharge across the discharge gap 82 to the second electrode 52.

The impedance seen by the high voltage power source and capacitor bank at node 214 of the circuit in FIG. 14 is determined primarily by the impedance of switching device 206 when the switching device is not conducting. When switching device 206 is not conducting, the impedance of the switching device 206 is sufficient to hold off the voltage from the high voltage power source—that is, to prevent conduction and discharge of the energy stored in capacitor bank 204. The capacitor bank 204 should have the ability to withstand the voltage from the high voltage power source and provide enough capacitance to store a suitable amount of energy to produce the requisite current flow in the gap. In experiments, capacitor banks totaling approximately 0.015-0.03 µF have been used with an overall ratings ranging from 35-70 kV (made up by series and parallel combinations of high voltage capacitors). But, these values should only be considered exemplary and not limiting. When the switching device 206 is conducting the impedance of switching device 206 is comparable to or less than the plasma impedance in the discharge gap. By way of example, and not limitation, in certain embodiments consistent with the invention, the voltage at test point 214 is in the range of several tens of kV (e.g., 35 kV), and the capacitor bank 204 is charged to this high voltage level. When the switching device 206 is off, it is preferable that no significant current passes through the switching device 206 and the switching device 206 has an impedance that is very high and is in fact essentially an open circuit. At the voltage levels used in conjunction with certain embodiments, this is no small task as the switch must neither conduct or arc when tens of kV are applied across its terminals. When on, the switching device 206 may have an "on" impedance in the range of several tens or hundreds of ohms, and is preferably as low as possible. In comparison, the plasma in the discharge gap 82 may have an impedance during conduction on the order of about one hundred ohms (for example).

The dielectric 56 used in the gap 82 can be any dielectric material with thickness and dielectric strength sufficient to withstand the applied voltage without breaking down. Successful experiments have been carried out using various grades of alumina ($Al_2O_3$), Macor, and Polyimide films having thicknesses ranging from 0.005 inches to 0.07 inches.

The formation of a plasma in the discharge gap results in a lowering of the resistance across the discharge gap and subsequently in an increase in the amount of charge transferred across the discharge gap. The increased charge transfer subsequently results in a drop in the gap voltage across gap 82 as charge builds up on the dielectric barrier material. Once the gap voltage falls below the ionization potential of the gap media, the plasma discharge is terminated. At this point, any residual charge is dissipated through the recovery circuit 208.

Figure 15:
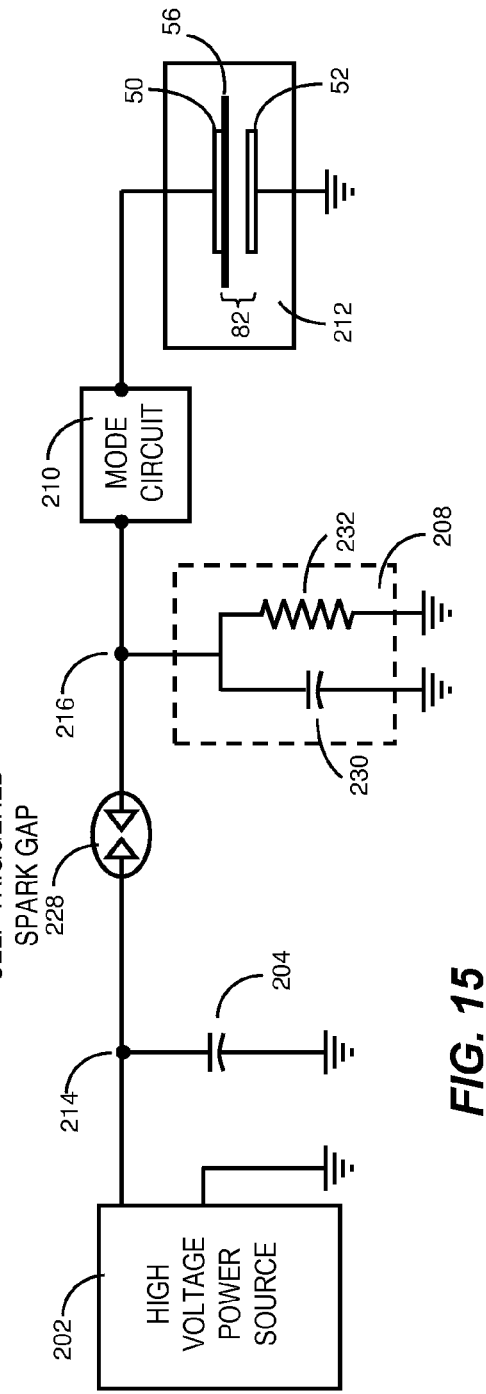
FIG. 15 is a block diagram of an alternative embodiment of generating a fast rise time output voltage step utilizing a self triggered spark gap.

FIG. 15 shows another embodiment of generating fast voltage rise times, with high current capabilities for plasma generation in dielectric barrier discharge plasmas where the switching device is a self triggered spark gap 228. The self-triggered spark gap triggers and becomes conducting when the voltage difference between the load side test point 216 and the supply side test point 214 is greater than the threshold voltage of the self triggered spark gap. Upon triggering the voltage at the load side test point 216, the voltage at the first electrode 50 rises fast enough to generate an overvoltage condition prior to expiration of the ionization lag time and subsequently a plasma discharge is created across the discharge gap. In prototype embodiments, suitably rated commercially available PerkinElmer™ Optoelectronics (Fremont, Calif.) overvoltage spark gap models OGP-75-22 and OGP-75-24 self discharging spark gap were successfully used with the voltage across the spark gap rising to 22 or 24 kV respectively at which point the spark gap 228 conducted initiating the plasma generation in the gap 82.

The rise in the voltage at the load side test point 216 causes the voltage difference between the load side test point 216 and the supply side test point 214 to fall well below the threshold voltage of the self triggered spark gap 228, and subsequently the self triggered spark gap 228 stops conducting. The voltage at the load side test point 216 is maintained by the charge on the dielectric 56; therefore, to get the self-triggered spark gap 228 to conduct again, the recovery circuit 208 is used to lower the voltage at the load side test point 216.

The recovery circuit 208 may have any suitable network of passive or active electronic components (e.g., resistors, capacitors, and/or inductors) which serve to bleed-off the voltage at the load side test point to ground. One simple embodiment of the recovery circuit, as illustrated in FIG. 15, uses a recovery capacitor 230 and a recovery resistor 232 in parallel with each other and connected between the load side test point and ground. This particular embodiment of recovery circuit 208 lowers the load side voltage over a time period characterized by the RC time constant of the recovery resistor 232 and recovery capacitor 230. The characteristic RC time constant in this embodiment of the recovery circuit subsequently controls the length of time between triggering events when the self triggered spark gap is used as the switching device. It is noted that stray impedances may also factor into the recovery time.

Of course, those skilled in the art will appreciate that the components used for elements 230 and 232 should be rated to withstand the high instantaneous voltage levels from node 216 to ground to avoid damage to the components. In experiments, values of resistor 232 ranging from about 1 to 4 megaohm have been used in conjunction with capacitor 230 ranging from about 100 to 700 picofarads to produce RC time constants in the range of 0.1 to 3 milliseconds, but of course, these values are merely illustrative of those used in experiments conducted and are not to be considered limiting in any way.

Figure 16:
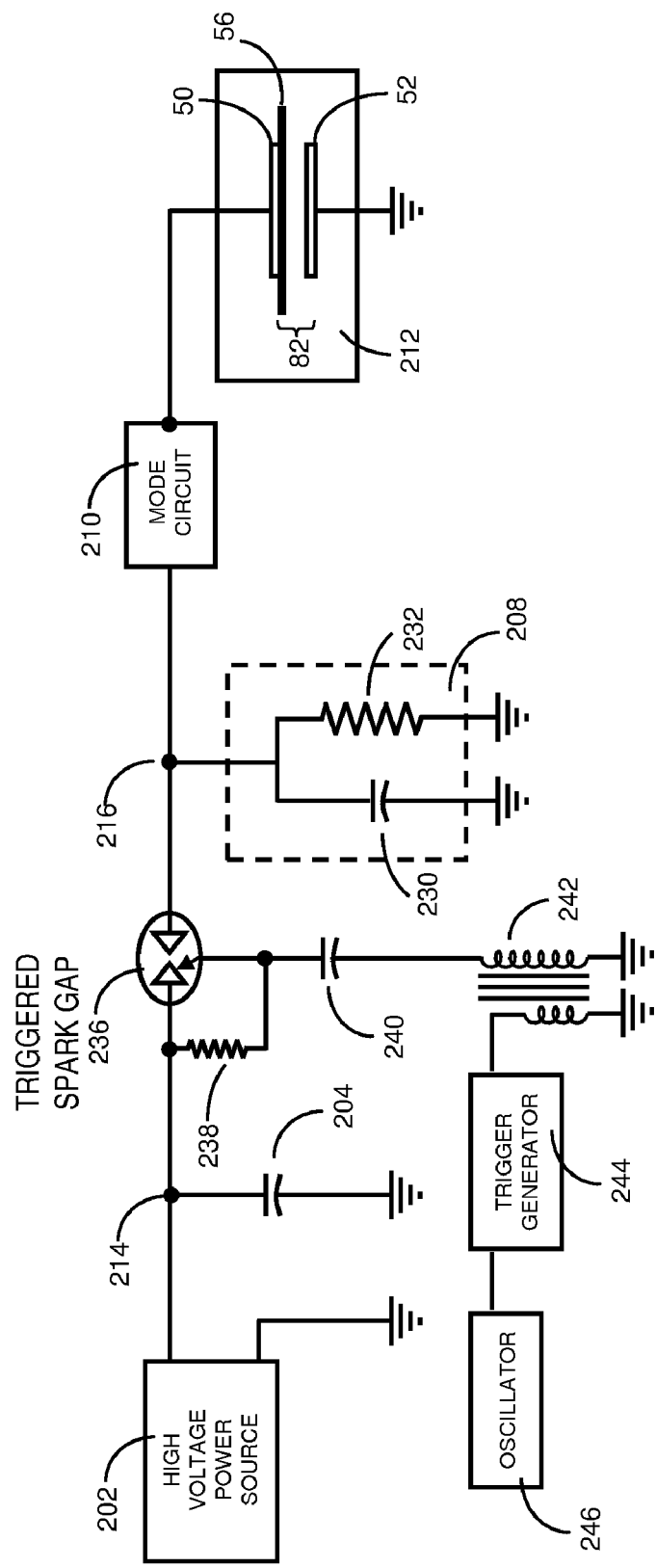
FIG. 16 is a block diagram of an alternative embodiment of generating a fast rise time output voltage step utilizing a triggered spark gap.

FIG. 16 shows another embodiment of a device for generating fast voltage rise times, with high current capabilities for plasma generation in dielectric barrier discharge plasmas where the switching device used is a triggered spark gap 236. In prototype embodiments, a commercially available PerkinElmer™ Optoelectronics brand triggered spark gap model GP-14B was successfully used. In the embodiment of FIG. 16, a tunable oscillator circuit 246 is used to drive a trigger generating circuit 244 which produces a pulsed signal through a triggering transformer 242 (commercially available PerkinElmer™ Optoelectronics model TR-1855) and a high voltage blocking capacitor 240 to cause the triggered spark gap switching device 236 to begin conducting if the voltage difference between the supply side test point 214 and the load side test point 216 is greater than the minimum operating voltage of the triggered spark gap. Transformer 242 is used to increase the output of the trigger generator to a voltage level adequate to assure switching of the spark gap from the off state (non-conducting) to the on state (conducting). A trigger resistor 238 is connected between the trigger electrode of the triggered spark gap 236 (at the junction of the capacitor 240) and the source side electrode 214 to establish a zero DC voltage on the trigger electrode.

The embodiments of recovery circuit 208 used to lower the voltage at the load side test point when the self triggered spark gap 228 is used as the switching device are also suitable when the triggered spark gap 236 is used as the switching device 206. In the embodiment depicted in FIG. 16, the RC time constant of the recovery circuit determines the time at which the threshold voltage across the triggered spark gap 236 will be high enough to enable it to begin conducting again. The length of time between triggering events for the embodiment depicted in FIG. 16 may be set to any time equal to or greater than the recovery time characterized by the RC time constant of the recovery circuit.

Those skilled in the art will appreciate upon consideration of the present teachings that in any of these embodiments, the high voltage power source 202 can be devised to provide either a positive or negative voltage with respect to ground so that the storage capacitor banks are either positively charged or negatively charged to generate either positive or negative output voltage steps that are ultimately delivered to the gap 82.

Figure 17:
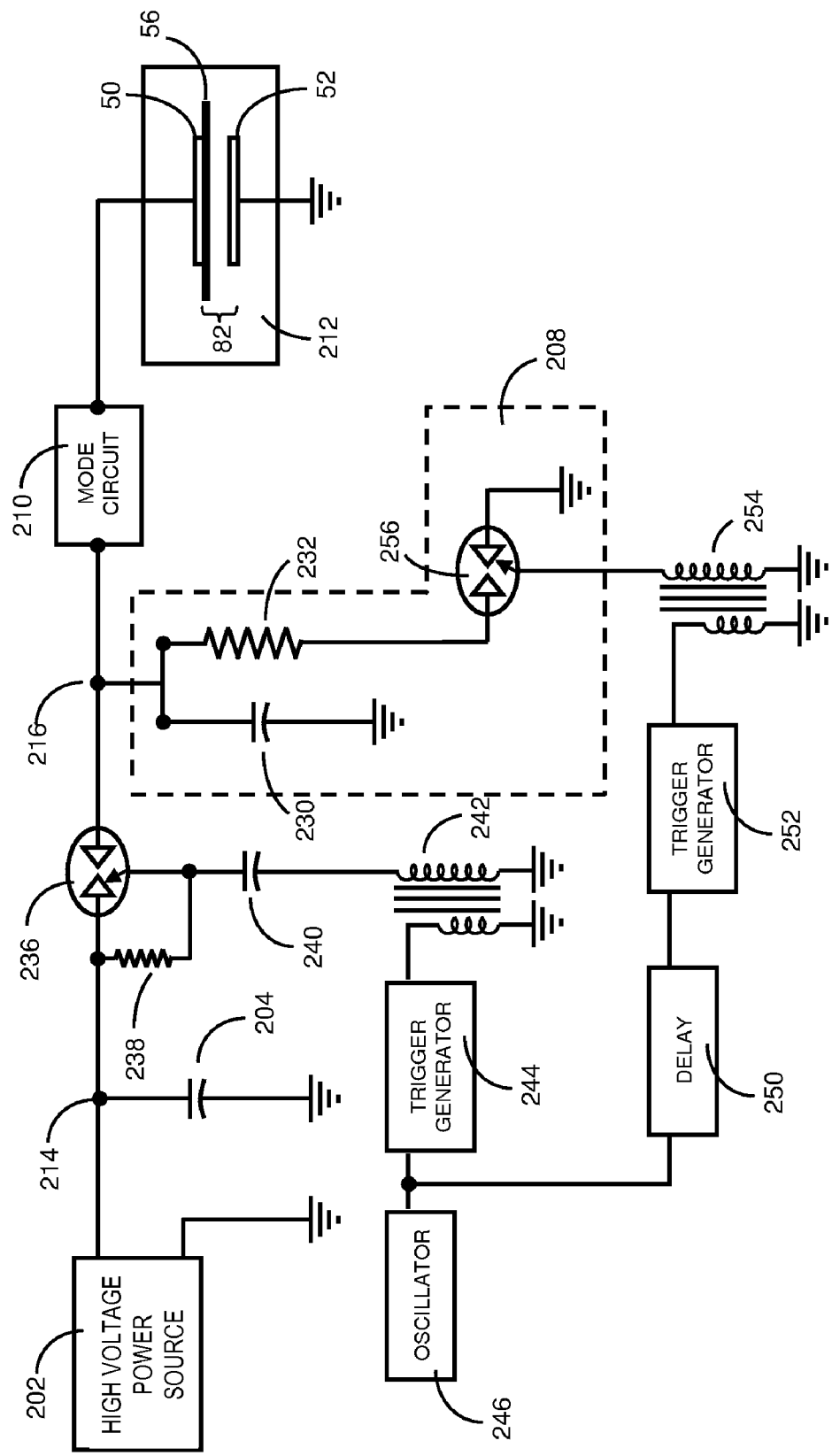
FIG. 17 is a block diagram of an alternative embodiment of generating a fast rise time output voltage step utilizing more than one triggered spark gap.

Other embodiments for generating fast voltage rise times, with high current capabilities for plasma generation in dielectric barrier discharge plasmas include the use of the tunable oscillator circuit to regulate the flow of charge through other circuit components along with the triggered spark gap. For example, in the embodiment of FIG. 17, the bleed off of voltage at the load side test point 216 through the recovery circuit 208 can be timed to occur once the triggered spark gap 236 stops conducting. In this embodiment a delay circuit 250, is attached between the tunable oscillator circuit 246 (e.g., a variable oscillator that can be varied in frequency over any suitable range of frequencies so that the plasma generation cycles are complete from discharge through a state wherein the charge on the dielectric 56 is suitably drained) and a second trigger generator circuit 252. After some predefined period of time defined after triggering of the trigger generator 244 defined by the delay of circuit 250 the second trigger generator circuit 252 causes a second triggering transformer 254 (used to assure that the trigger voltage from the trigger generator 252 is boosted to a voltage level adequate to assure triggering of the spark gap 256 from the off state to the on state) to send a pulse to enable a second triggered spark gap 256 to begin conducting. The conduction through the second triggered spark gap 256 enables the voltage at the load side test point 216 to be bled off to ground thereby discharging any residual charge on the dielectric 56.

Figure 18:
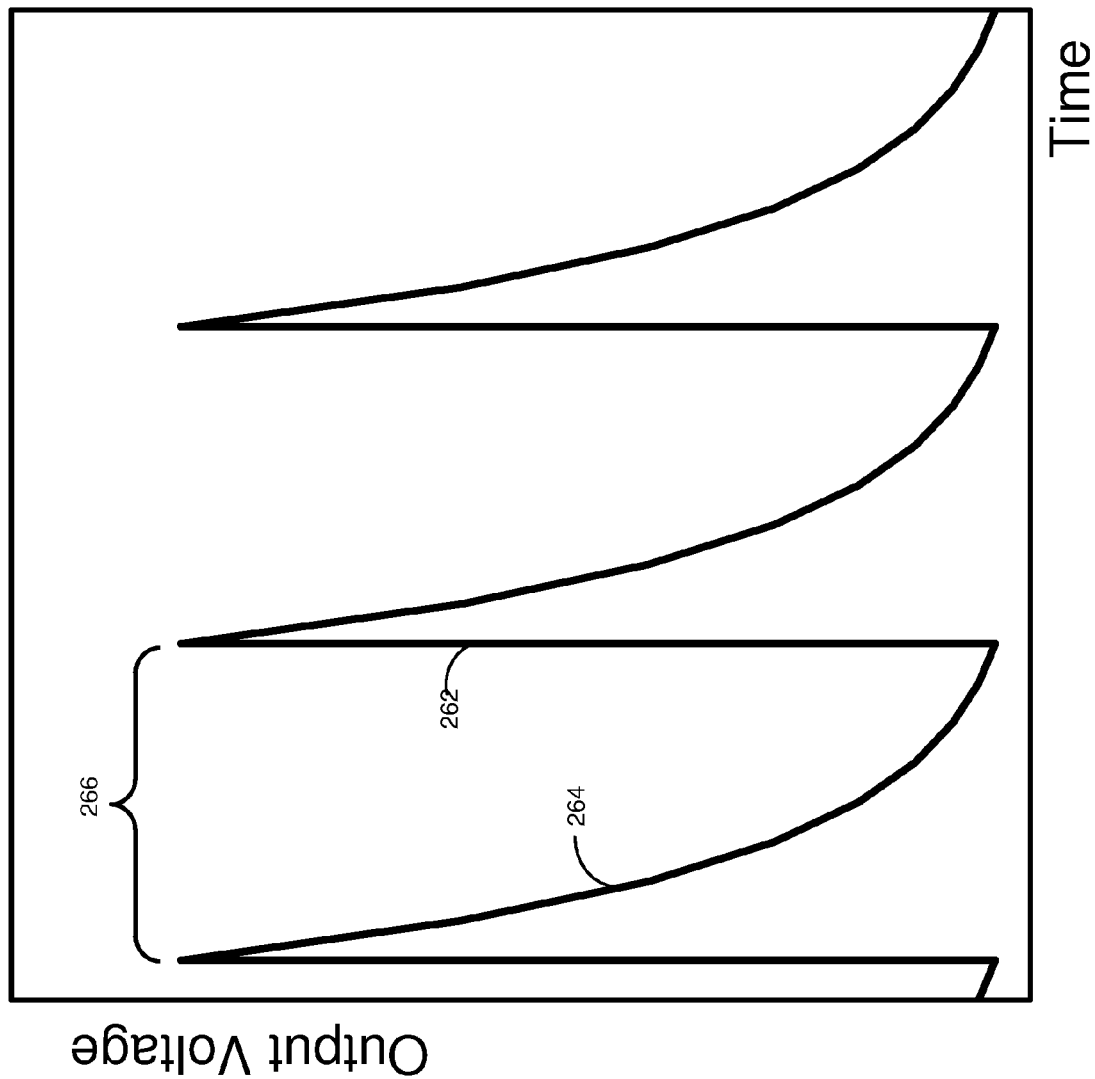
FIG. 18 is a trace of output voltage with a repetition rate set near its maximum.

FIG. 18 shows a typical waveform for the output voltage at the first electrode in the embodiment of FIG. 16 as a function of time. The output voltage for the embodiment in FIG. 16 is characterized by a rise time 262 sufficiently short to support the generation of an overvoltage within the lag time. Following the rise in voltage and a current pulse, the switching device 236 stops conducting and the recovery circuit 208 begins bleeding of the voltage causing a voltage recovery 264 in the output waveform. The length of time between two rise times defines a pulse period 266. The minimum length of time for the pulse period is determined by the recovery circuit and may be as small as microseconds in certain embodiments.

Figure 19:
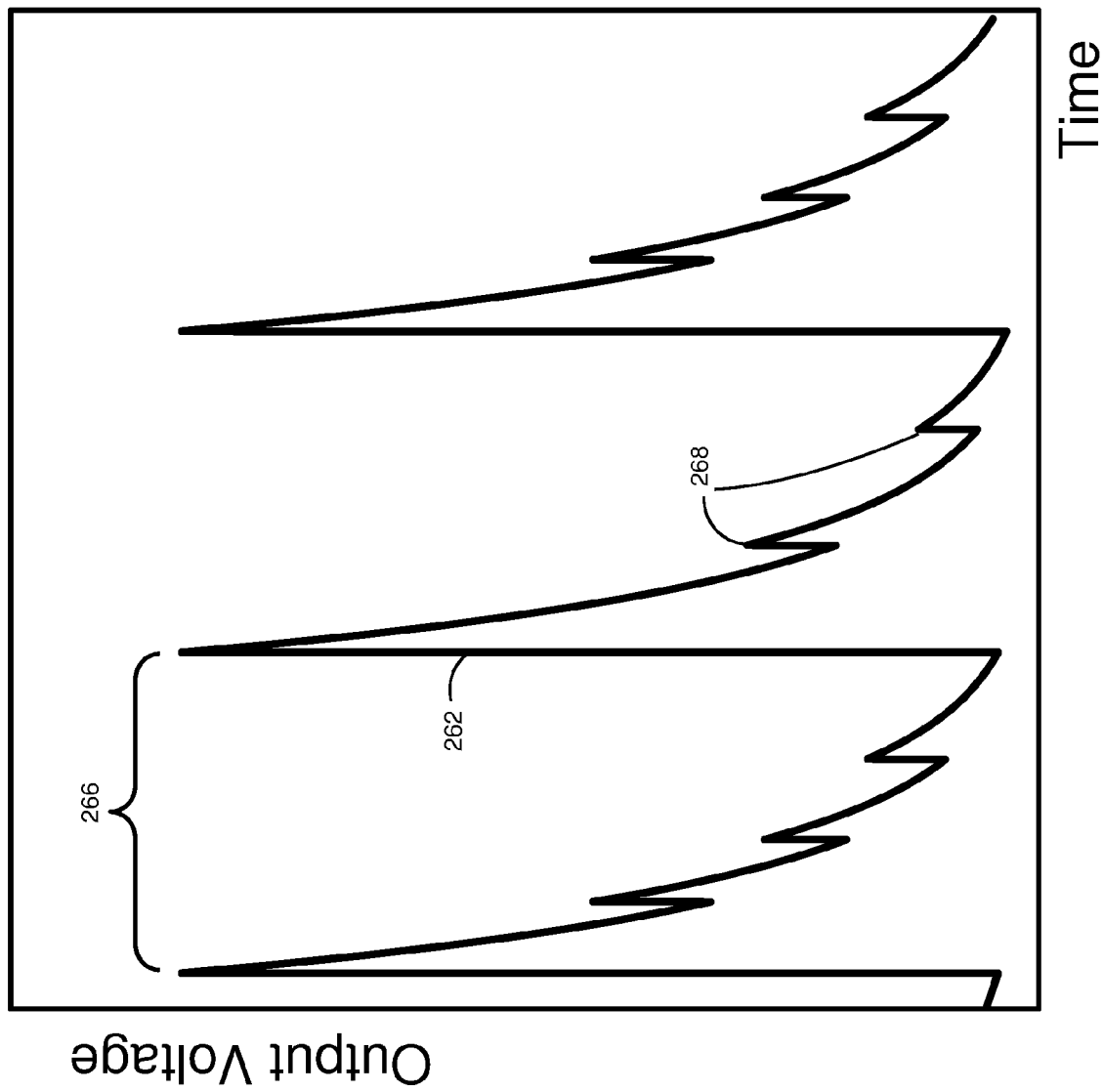
FIG. 19 is a trace of output voltage with a repetition rate set near its maximum and reverse discharges occurring after the initial plasma discharge.

The output voltage at the first electrode may contain one or more reverse discharge spikes 268 as shown in FIG. 19 if the discharge gap is sufficiently small to support reverse discharges in the gap media. The reverse discharge spikes occur when the voltage build up on the dielectric becomes large enough to support the formation of a plasma discharge or microdischarges across the discharge gap. The reverse discharge spikes provide a possible mechanism of reducing residual charge which can otherwise accumulate on the surface of the dielectric barrier material. The reverse direction plasma discharges are generally smaller and can be controlled by adjusting the neutral gas density between the electrodes 50 and 52 through changes in operating temperature and pressure.

Figure 20A:
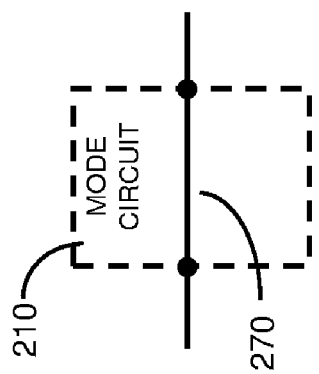
FIG. 20, which is made up of FIGS. 20A, 20B and 20C, shows a block diagram outlining a few basic embodiments of the mode circuit consisting of (a) a short, (b) a resistance network, and (c) a capacitor and resistor network.
Figure 20B:
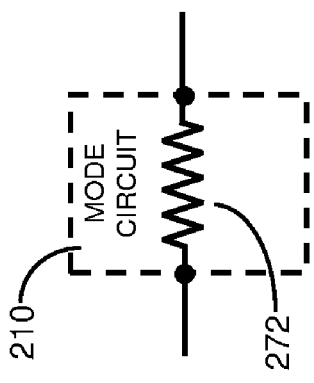
Figure 20C:
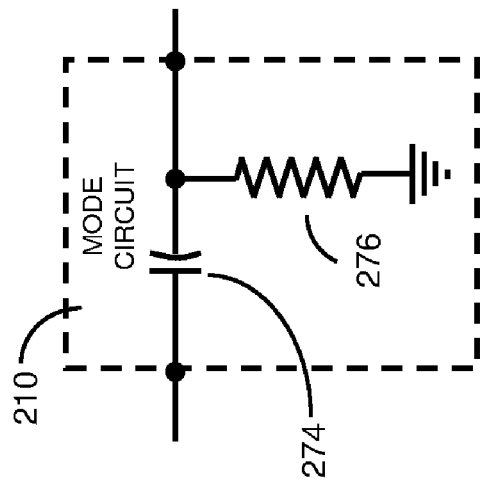

The mode circuit 210 can be fabricated of any network of passive or active electronic components (resistors, capacitors, and/or inductors) which serve to modify the impedance between the load side test point and the first electrode and in turn enable the total voltage and discharge current characteristics to be controlled. The waveform of the current transported through the plasma discharge is shaped through the mode circuit. A shorted mode circuit 70 as show in FIG. 20A serves to minimize the impedance and maximize the magnitudes of the output current to produce a spiked current profile 284 as depicted in FIG. 21B. The shorted mode circuit produces high instantaneous currents with a spike width 280 that is on the order of 1-500 ns. A resistor mode circuit 272 as shown in FIG. 20B increases the impedance causing the magnitude of the plasma current to decrease while substantially lengthening the time period of the plasma discharge leading to a pedestal or exponential current profile 286 as depicted in FIG. 21C. In a third possible embodiment of the mode circuit a mode capacitor 274 can be used to reduce the maximum voltage applied to the discharge gap and a recovery mode resistor 276 is used to bleed-off the voltage from the added capacitor and the first electrode before the next voltage step. Additional embodiments may be tailored to the specific current/voltage profile most beneficial to a desired application. FIG. 21 compares the spiked current profile in FIG. 21B to the pedestal current profile of FIG. 21C for an input voltage waveform with rise time 262 and a lag time 282 as depicted in FIG. 21A sufficient to produce an overvoltage across the discharge gap during the lag time.

The dielectric barrier circuits embodied in FIGS. 14-17 have a planar geometry for both the first electrode 50 and the second electrode 52, but other geometries are also suitable including cylindrical geometries, spherical geometries, or any other geometry/combination of geometries where two conducting electrodes are separated by a discharge gap. The dielectric barrier circuits embodied in FIGS. 14-17 have the dielectric barrier material attached to the first electrode 50, but other placements of the dielectric barrier 56 are also suitable such that the dielectric barrier material 56 is placed somewhere between the first electrode 50 and second electrode 52. Similarly, the shape of the dielectric barrier material is not limited to a planar geometry and can take other shapes including but not limited to cylindrical tubes, spheres, coatings, and flexible films. The dielectric barrier material embodied in FIGS. 14-17 is illustrated as a single layer, but other suitable embodiments include the use of one or more layers composed of one or more materials and/or material composites. Embodiments incorporating more than one dielectric barrier material in the discharge gap are also suitable.

Figure 22:
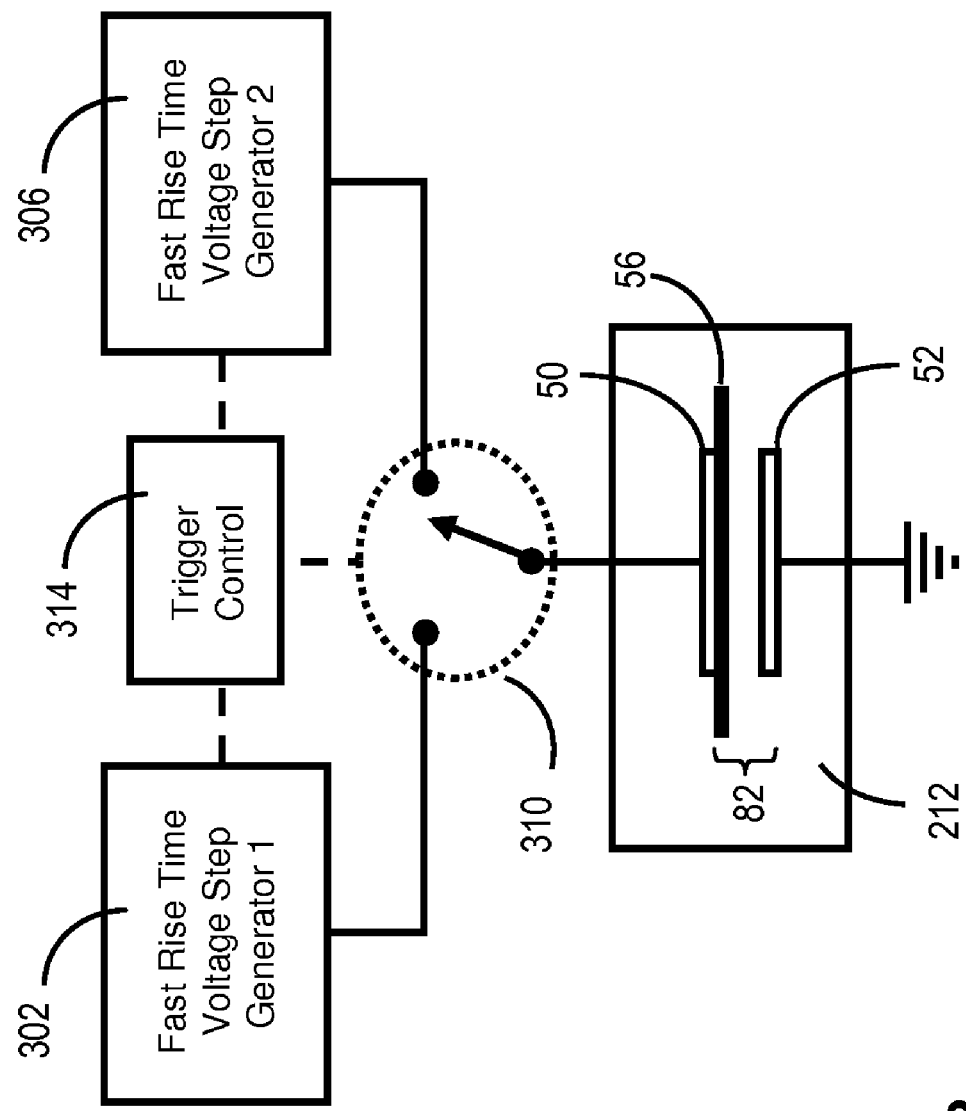
FIG. 22 is a block diagram depicting an embodiment used for alternation of the polarity of the output step in a manner consistent with certain embodiments.

Numerous variations in the embodiments described are possible without departing from the present invention. FIG. 22 shows a simplified block diagram of one such embodiment in which two storage capacitor banks are used to generate either positive or negative output voltage steps. This can be accomplished in any number of ways including use of multiple high voltage power sources and alternating therebetween or by alternating the polarity of the high voltage power source's output terminals on alternating cycles or by use of a plurality of storage capacitor banks are used to controllably switch between either positive or negative output voltage steps. In this example, two fast rise time voltage step generators are used to create an overvoltage plasma. The voltages supplied by generators 302 and 306 may be both positive, both negative, or one may be positive and the other negative. In this embodiment a control switch 310 is used to keep the generators from supplying voltages to each other and to isolate the output of the generators to the electrodes of the dielectric barrier discharge. In this embodiment a trigger control 314 is used to manage when the generators create a step voltage with regard to each other and the position of the control switch 310.

Figure 23:
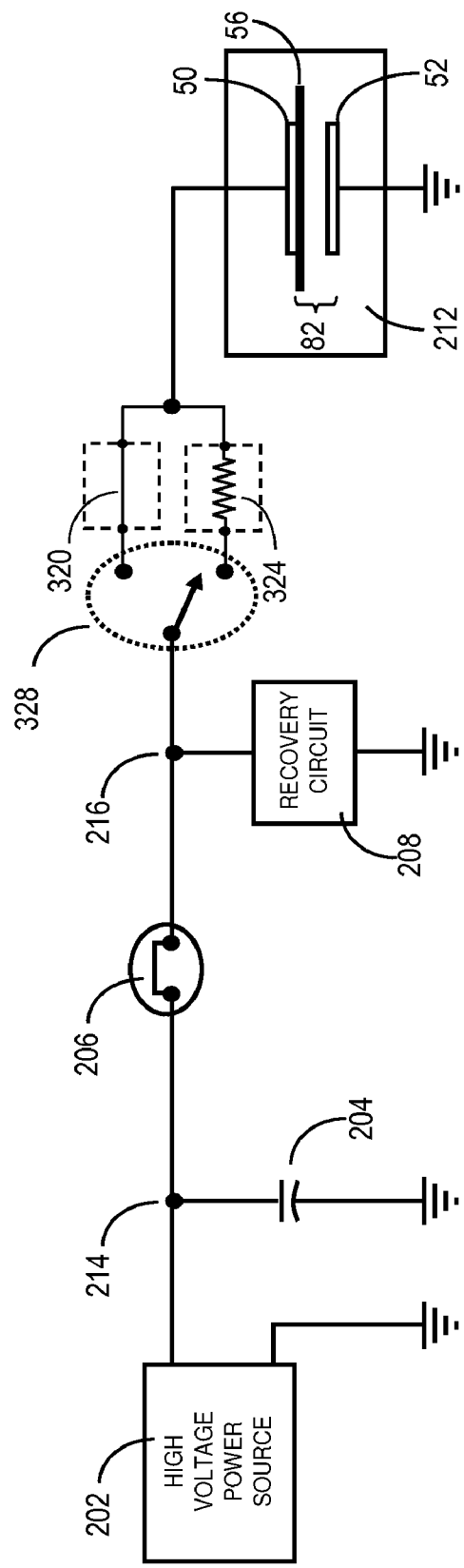
FIG. 23 is a block diagram depicting use of multiple mode circuits in order to control characteristics of the discharge current in a manner consistent with certain embodiments.

Another variant is depicted in FIG. 23 wherein multiple mode circuits are used to adjust the width, amplitude, or decay of the discharge current by switching between the multiple mode circuits. In this exemplary embodiment, two such different mode circuits 320 and 324 are individually selected by a switch 328 to select the desired mode. Additional embodiments may contain more than two mode circuits and/or may contain more than one switch to provide selectivity between different modes. In addition, the switch may be switched manually or in accord with a switch control mechanism (not shown) so that the mode circuit switching can be controlled during the time of the discharge to dynamically change the discharge properties in accord with any of a number control parameters as desired for the particular application. So, for example, the mode circuits can be switched after a specified delay from the step. Or, the mode may be switched by use of a delay and trigger generator as is used to control the recovery circuitry as previously shown. Many variations will occur to those skilled in the art upon consideration of the present teachings.

In embodiments such as those presented, uniform glow discharges with an apparent absence of filamentary discharges have been obtained using a variety of gases and pressures in the gap, including air with pressures up to and including atmospheric pressures and beyond. Uniform, non-filamentary atmospheric pressure discharges are advantageous in many applications since objects being treated may not have to first undergo a process of evacuation of the gap area down to low pressures. One example being the sterilization processes described above wherein the plasma can provide sterilization without need for special gases or pressures.

The spark gap switching devices used in prototypes are commonly used in high voltage crowbar type circuits which are used to prevent damage to power source loads in the event of a malfunction of a power source. While spark gaps used as switches in the current embodiments have been found effective, other switching devices may also be utilized provided the switch has an internal impedance less than or on the order of the load impedance when the switch is closed and is capable of passing currents, for example, of a of amperes or kiloamperes and greater when the switch is closed, and capable of standing-off sufficient voltage to create the overvoltage when the switch is open, and has a suitably fast switching time.

For reasons of economy the present discussion has emphasized air or nitrogen as the working gases in the gap, although, glow-like discharges have been produced with embodiment of the present invention device in Nitrogen, Oxygen, Sulfur Hexafluoride ($SF_6$), Carbon Tetrafluoride $CF_4$), Helium, Neon, Argon, Krypton, Acetylene ($C_2H_2$), Titanium Tetrachloride ($TiCl_4$), and mixtures of some of the previously mentioned gases. For comparison, the highest instantaneous power densities in nitrogen gas in a glow-like DBD have been reported by Golubovskii (~2 kw/cm$^2$). The highest value observed using techniques described in this application is approximately 50 times as high at approximately 100 kW/cm$^2$.

Thus, in certain embodiments, a method of generating a fast-rise time voltage step to produce an overvoltage condition for a dielectric barrier plasma discharge involves providing a pair of electrodes spaced apart by an electrode gap and having one or more dielectrics disposed in the electrode gap; generating the fast-rise time voltage step such that the rise time to achieve the overvoltage condition is equal to or less than the time required to generate the plasma thereby establishing the overvoltage condition prior to current flow across the electrode gap; generating an output power from storage capacitor banks that discharge into the electrode gap through a switch with an internal impedance less than the load impedance when the switch is closed, capable of passing the gap currents, typically amperes or a kiloampere or greater when the switch is closed, and capable of standing-off sufficient overvoltage potentials when the switch is open; and generating a discharge current pulse across the electrode gap that is terminated by the charging properties of the dielectric(s) in the electrode gap.

In certain embodiments, a recovery circuit to reduce the magnitude of the voltage on the dielectric after the generation of each voltage step. In certain embodiments, the generation of voltage steps and the subsequent recovery of the voltage to a prior voltage state constitutes a discharge cycle and a repetition frequency of these cycles is established. In certain embodiments, a mode circuit made up of resistors, inductors, and/or capacitors is placed in series and/or parallel with the electrode gap to control the total width, amplitude, or decay of the discharge current In certain embodiments, the width, amplitude, or decay of the discharge current can be changed by switching between multiple mode circuits comprising resistors, inductors, and/or capacitors in series and/or parallel with the electrode gap. In certain embodiments, the total internal source impedance is less than the discharge impedance, thereby delivering the maximum available power on every cycle and producing an output current that scales proportionally with electrode area. In certain embodiments, the storage capacitor banks are either positively charged or negatively charged to generate either positive or negative output voltage steps. In certain embodiments, more than one storage capacitor bank is used to controllably switch between either positive or negative output voltage steps. In certain embodiments, the initial plasma discharge is followed by one or more than one smaller reverse direction plasma discharges that assist in the removal of charges from the dielectric. In certain embodiments, the reverse direction plasma discharges are controlled by adjusting the neutral gas density between the electrodes through changes in operating temperature and pressure. In certain embodiments, the overvoltage condition produces runaway electrons in the plasma discharge. In certain embodiments, runaway electrons have sufficient energy to produce x-rays. In certain embodiments, a shock wave is created in the plasma by the deposition of power in a working gas over a time period shorter than the acoustic transit time in the working gas. In certain embodiments, the initial plasma discharge is followed by at least one smaller reverse direction plasma discharge that assists in the removal of charges from the dielectric In another embodiment, a method of generating a fast-rise time voltage step to produce an overvoltage condition for a dielectric barrier plasma discharge involves providing a pair of electrodes spaced apart by an electrode gap and having one or more dielectrics disposed in the electrode gap; generating the fast-rise time voltage step such that the rise time to achieve the overvoltage condition is equal to or less than the time required to generate the plasma thereby establishing the overvoltage condition prior to current flow across the electrode gap; generating an output power from storage capacitor banks, which discharges rapidly into the electrode gap through a spark gap that self triggers when a voltage differential across the spark gap is above a characteristic threshold voltage of the spark gap; generating an output current pulse across the electrode gap that is terminated by the charging properties of the dielectric(s) in the electrode gap.

In certain embodiments, a recovery circuit is used to reduce the magnitude of the voltage on the dielectric after the generation of each voltage step. In certain embodiments, the generation of voltage steps and the subsequent recovery of the voltage to a prior voltage state constitute a discharge cycle and a repetition frequency of these cycles is established. In certain embodiments, the width, amplitude, and decay of the discharge current can be switched between multiple combinations of resistor, inductor, and/or capacitance networks in series or parallel with the generator output. In certain embodiments, the storage capacitor banks are either positively charged or negatively charged to generate either positive or negative output voltage steps. In certain embodiments, more than one the storage capacitor bank is used to controllably switch between either positive or negative output voltage steps.

In another embodiment, a method of generating a fast-rise time voltage step to produce an overvoltage condition for a dielectric barrier plasma discharge involves providing a pair of electrodes spaced apart by an electrode gap and having one or more dielectrics disposed in the electrode gap; generating the fast-rise time voltage step such that the rise time to achieve the overvoltage condition is equal to or less than the time required to generate the plasma thereby establishing the overvoltage condition prior to current flow across the electrode gap; generating an output power from storage capacitor banks, which discharges rapidly into the electrode gap through a triggered spark gap that controllably generates voltage steps when a secondary circuit provides a sufficient signal to enable current flow through the triggered spark gap; generating an output current pulse across the electrode gap that is terminated by the charging properties of the dielectric (s) in the electrode gap.

In certain embodiments, a recovery circuit to reduce the magnitude of the voltage on the dielectric after the generation of each voltage step. In certain embodiments, the generation of voltage steps and the subsequent recovery of the voltage to a prior voltage state constitute a discharge cycle and a repetition frequency of these cycles is established. In certain embodiments, the width, amplitude, and decay of the discharge current can be switched between multiple combinations of resistor, inductor, and/or capacitance networks in series or parallel with the generator output. In certain embodiments, the storage capacitor banks are either positively charged or negatively charged to generate either positive or negative output voltage steps. In certain embodiments, more than one storage capacitor bank is used to controllably switch between either positive or negative output voltage steps.

In certain embodiments, an apparatus for generating a fast-rise time voltage step to produce an overvoltage condition for a dielectric barrier plasma discharge has a pair of electrodes spaced apart by an electrode gap and having one or more dielectrics disposed in the electrode gap. A storage capacitor is provided. A high voltage power generator charges the storage capacitor to a voltage level adequate to produce an overvoltage condition across the electrode gap. A switch couples the storage capacitor to the electrode gap, the switch having an open state and a closed state. Wherein, the switch when in the open state is able to hold back a voltage level adequate to produce an overvoltage condition across the electrode gap and the switch when in the closed state is able to withstand current passing through the plasma generated in the electrode gap, and the switch's switching time from the open state to the closed state is less than the lag time for plasma discharge across the electrode gap, so that switching the switch from the open state to the closed state generates the fast-rise time voltage step such that the rise time to achieve the overvoltage condition is equal to or less than the time required to generate the plasma thereby establishing the overvoltage condition prior to current flow across the electrode gap. When the switch is switched from the open state to the closed state, an output current pulse is generated across the electrode gap that is terminated by charging properties of the dielectric in the electrode gap.

In certain embodiments, the switch can be a spark gap switch. In certain embodiments, the switch can be either one of a self triggering spark gap switch and a triggered spark gap switch. In certain embodiments, a recovery circuit is used to reduce the magnitude of the voltage on the dielectric after the generation of the voltage step. In certain embodiments, the generation of the voltage step and the subsequent recovery of the voltage to a prior voltage state constitutes a discharge cycle, and further a circuit is provided for repeatedly establishing the discharge cycle at a repetition frequency. In certain embodiments, a mode circuit is coupled to at least one of the electrodes to control the total width, amplitude, or decay of the discharge current pulse.

In another embodiment, an apparatus for generating a fast-rise time voltage step to produce an overvoltage condition for a dielectric barrier plasma discharge has a pair of electrodes spaced apart by an electrode gap and having one or more dielectrics disposed in the electrode gap. A storage capacitor is provided. A high voltage power generator charges the capacitor to a voltage level adequate to produce an overvoltage condition across the electrode gap. A spark gap switch couples the storage capacitor to the electrode gap, the switch having an open state and a closed state. The switch when in the open state is able to hold back a voltage level adequate to produce an overvoltage condition across the electrode gap, and the switch when in the closed state is able to withstand current passing through the plasma generated in the electrode gap. The switch's switching time from the open state to the closed state is less than the lag time for plasma discharge across the electrode gap, so that switching the switch from the open state to the closed state generates the fast-rise time voltage step such that the rise time to achieve the overvoltage condition is equal to or less than the time required to generate the plasma thereby establishing the overvoltage condition prior to current flow across the electrode gap. When the switch is switched from the open state to the closed state, an output current pulse is generated across the electrode gap that is terminated by charging properties of the dielectric in the electrode gap. A recovery circuit reduces the magnitude of the voltage on the dielectric after the generation of the voltage step.

In certain embodiments, the switch can be a self triggering spark gap switch. In certain embodiments, the switch can be a triggered spark gap switch; and the generation of the voltage step and the subsequent recovery of the voltage to a prior voltage state constitutes a discharge cycle; and an oscillator establishes the discharge cycle at a repetition frequency, and which triggers the triggered spark gap switch at the repetition frequency.

A method of generating a fast-rise time voltage step to produce an overvoltage condition for a dielectric barrier plasma discharge involves providing a pair of electrodes spaced apart by an electrode gap and having one or more dielectrics disposed in the gap; generating fast-rise time voltage step such that the rise time to achieve the overvoltage condition is equal to or less than the time required to generate the plasma thereby establishing the overvoltage condition prior to current flow across the electrode gap. Power from storage capacitor banks discharge into the electrode gap through a switch. The switch is capable of standing-off voltage sufficient to create the overvoltage condition when the switch is open. The discharge current pulse across the electrode gap is terminated by charging properties of the dielectric(s) in the electrode gap.

Hence, certain of the various embodiments address a problem of generating fast voltage rise times, with current capabilities in excess of kiloamperes, across the electrode gap of a dielectric barrier discharge without the use of Blumleins by making use of the self-terminating behavior of dielectric barrier discharges. Thus, the scalability of the output power with electrode area is improved by generating fast rise time voltage steps for dielectric barrier discharges with internal circuit impedances less than the load impedance of the gap during discharge, thereby eliminating the need to match the impedance during differing applications and loads. In experiments conducted using the above circuits, a range of about 11 $cm^2$ to about 100 $cm^2$ has been used for electrode areas without need for adjustment in the circuit parameters. Hence, the same circuitry can be quite readily adapted to a wide range of uses without substantial modification to tune the circuit as would be required in traditional Blumlein circuits.

In accordance with certain embodiments, various attributes of the plasma discharge have been observed and these can be enhanced to suit the requirements for particular applications. By way of example, and without any suggestion that any or all of the present attributes are necessary conditions which are present in any given embodiment, the following observations (and associated theories, to which the presently claimed invention is not to be bound) are presented:

The sharp rise time which produces the extreme overvoltage increases the average electron energy and under some conditions may produce high energy runaway electrons.

The runaway electrons produced under extreme overvoltage conditions may be used to generate x-rays from the plasma discharge.

A combined RF and pulsed power supply can potentially be used to achieve overvoltage conditions without altering the pulse generator. A synchronizer can be used for timing the generation of pulsed voltage so that pulses are applied at the most beneficial part of the RF voltage waveform. This combination increases the power to the pulses and increases the energy of the electrons.

The extreme overvoltage can produce a plasma discharge in any gaseous media over a range of pressures from a few atmospheres to a millitorr.

The extreme overvoltage can produce a plasma discharge at the surface of a liquid or porous media over a range of pressures from a few atmospheres to a millitorr.

The delivery of power to the media in the plasma discharge resulting from the over voltage condition produces a shock wave in the media. Shockwaves can be used to mix the media and mix solid particles in the discharge gap.

Embodiments consistent with the present invention may be well suited for a number of applications including but not limited to sterilization, deposition, etching, functionalization of surfaces, porous-like materials, and particles, dissociation of gases, abatement processes, ozone generation, generation of porous-like materials, x-ray generation, light emission, and laser emission.

Many variations will occur to those skilled in the art upon consideration of the present teachings. While certain embodiments herein were described in conjunction with specific circuitry that carries out the functions described, other embodiments are contemplated in which other circuitry can be used to carry out the functions described. As noted above, much of this discussion has involved theory of operation that has not yet been fully explored and proven, thus, the claims should not be restricted on the basis of the disclosed theory.

While certain illustrative embodiments have been described, it is evident that many alternatives, modifications, permutations and variations will become apparent to those skilled in the art in light of the foregoing description.

What is claimed is:

1. A method of generating a glow discharge plasma, comprising:
    providing a pair of electrodes spaced apart by an electrode gap, and having a dielectric disposed in the electrode gap between the electrodes;
    placing the electrodes within an environment where the electrode gap is provided with a gas at a specified pressure;
    applying a voltage pulse having a rapid rise time across the electrodes to cause an extreme overvoltage condition, where the rapid rise time is less than a plasma generation time so that the extreme overvoltage condition occurs prior to current flow across the electrode gap; and where the plasma induces a change of a physical or chemical property of the gas.

2. The method according to claim 1, where the gas comprises a mixture of gasses.

3. The method according to claim 1, where change in the gas occurs via at least one of energy, free radicals, reactive species and electrons provided by a plasma.

4. The method according to claim 1, where a solid phase is provided in the plasma.

5. The method according to claim 1, where a liquid phase is provided in the plasma.

6. The method according to claim 1, where the change in the gas occurs at a temperature that is lower than that temperature in which the change would occur in the absence of the plasma.

7. The method according to claim 1, where the change in the gas is via a reaction which is endothermic.

8. The method according to claim 1, where the change in the gas occurs via at least one of oxidation and halogenations.

9. The method according to claim 1, where the gas contains oxygen and the change in the gas results in ozone production.

10. The method according to claim 1, where the change in the gas comprises stripping of a component from the gas.

11. The method according to claim 10, where the component comprises hydrogen.

12. The method according to claim 1, where the change in the gas occurs via polymerization.

13. The method according to claim 1, where the change in the gas generates gas phase, liquid phase or solid phase reaction products.

14. The method according to claim 1, where the specified pressure is approximately one atmosphere.

15. The method according to claim 1, where a solid having a surface is introduced into the plasma and where the change in the gas generates one or more reactive species that carry out a process of surface cleaning, surface functionalization, surface modification, etching, reactive ion etching, chemical vapor deposition, atomic layer deposition, or sterilization of the solid.

16. The method according to claim 15, where the plasma induces a reaction at the surface of the solid.

17. The method according to claim 15, where the solid object is exposed to the plasma to induce a reaction in the solid via at least one of energetic electrons, x-rays or UV radiation.

18. The method according to claim 1, where the change in the gas comprises removal of at least one substance considered to be an air pollutant.

19. The method according to claim 1, where the gas contains a halogen, hydrogen, a metal, an element of a semiconductor material and a hydroxyl group.

20. The method according to claim 1, where a solid covers at least one of the pair of electrodes.

21. A method of generating a glow discharge plasma, comprising:
    providing a pair of electrodes spaced apart by an electrode gap, and having a dielectric disposed in the electrode gap between the electrodes;
    placing the electrodes within an environment where the electrode gap is provided with a liquid;
    applying a voltage pulse having a rapid rise time across the electrodes to cause an extreme overvoltage condition, where the rapid rise time is less than a plasma generation time so that the extreme overvoltage condition occurs prior to current flow across the electrode gap to generate the plasma in the liquid; and where the plasma induces a change in a physical or chemical property of the liquid.

22. The method according to claim 21, where the liquid comprises a mixture of liquids.

23. The method according to claim 21, where the plasma induces a reaction in the liquid.

24. The method according to claim 21, where the liquid covers at least one electrode.

25. The method according to claim 21, where the liquid is provided as atomized droplets, a spray or a vapor with or without a dry carrier gas.

26. The method according to claim 21, where the change in the liquid occurs in the presence of a solid phase object.

27. The method according to claim 21, where a solid phase object is introduced into the gap and where the plasma induces a reaction at the surface of the solid.

28. The method according to claim 21, where a solid object is introduced into the gap and the solid object is exposed to the plasma to induce a reaction in the solid object via at least one of energetic electrons, x-rays or UV radiation.

29. The method according to claim 21, where a solid covers at least one of the pair of electrodes.

30. The method according to claim 21, where a gas phase is provided in the plasma.

* * * * *